US008005538B2

(12) United States Patent
Massengale

(10) Patent No.: US 8,005,538 B2
(45) Date of Patent: Aug. 23, 2011

(54) STIMULATING CATHETER

(75) Inventor: Roger Massengale, Mission Viejo, CA (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 12/133,269

(22) Filed: Jun. 4, 2008

(65) Prior Publication Data

US 2008/0300530 A1 Dec. 4, 2008

Related U.S. Application Data

(60) Provisional application No. 60/941,932, filed on Jun. 4, 2007.

(51) Int. Cl.
*A61N 1/30* (2006.01)

(52) U.S. Cl. ............................................ 604/21; 604/20

(58) Field of Classification Search .................... 604/20, 604/501, 21, 105, 164.02
See application file for complete search history.

(56) References Cited

U.S. PATENT DOCUMENTS

| | | | |
|---|---|---|---|
| 3,642,004 A | | 2/1972 | Osthagen et al. |
| 5,613,950 A | * | 3/1997 | Yoon .............................. 604/105 |
| 5,688,265 A | | 11/1997 | Citronowicz |
| 5,830,151 A | | 11/1998 | Hadzic et al. |
| 5,853,373 A | | 12/1998 | Griffith et al. |
| 5,976,110 A | | 11/1999 | Greengrass et al. |
| 6,350,253 B1 | * | 2/2002 | Deniega et al. .......... 604/164.02 |
| 6,361,532 B1 | | 3/2002 | Burek |
| 6,456,874 B1 | * | 9/2002 | Hafer et al. .................... 604/21 |
| 6,730,083 B2 | | 5/2004 | Freigang et al. |
| 7,004,923 B2 | | 2/2006 | Deniega et al. |
| 2004/0138562 A1 | * | 7/2004 | Makower et al. ............. 600/439 |

FOREIGN PATENT DOCUMENTS

| | | |
|---|---|---|
| WO | WO 01/05210 | 1/2001 |
| WO | WO 2004/062470 | 7/2004 |
| WO | WO2004/062470 A2 * | 7/2004 |

OTHER PUBLICATIONS

International Search Report and Written Opinion for International Application No. PCT/US2008/065807, date of mailing: Oct. 7, 2008, in 32 pages.

* cited by examiner

*Primary Examiner* — Theodore J Stigell
*Assistant Examiner* — Brandy C Scott
(74) *Attorney, Agent, or Firm* — Dority & Manning, P.A.

(57) ABSTRACT

An apparatus for delivery of a substance to an anatomical region in a body can include a catheter comprising a catheter body, and one or more electrically conductive elements supported by the catheter body and in electrical communication with one or more sources of electrical stimulus. The catheter body can comprise a lumen therein, a substantially closed distal end, and an infusion section configured to permit fluid to pass through the catheter body and that can have a length that is less than or equal to the length of the catheter body. In some embodiments, the apparatus can comprise a coiled member positioned within the lumen of the catheter body. The coiled member can comprise adjacent coils and can permit the uniform flow of the substance through one or more holes formed in the catheter body.

18 Claims, 9 Drawing Sheets

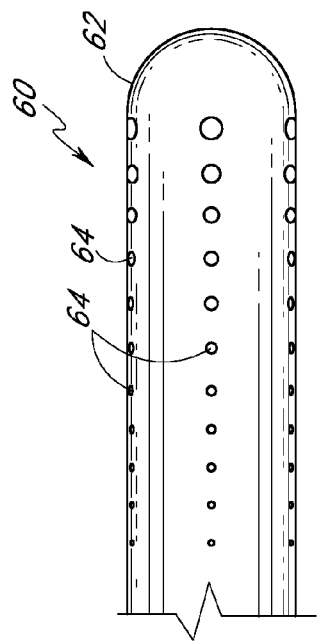
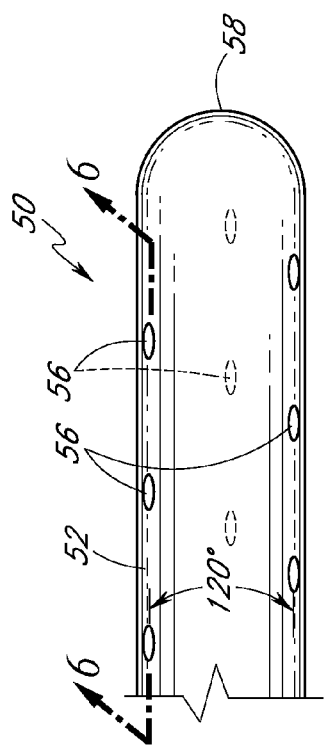
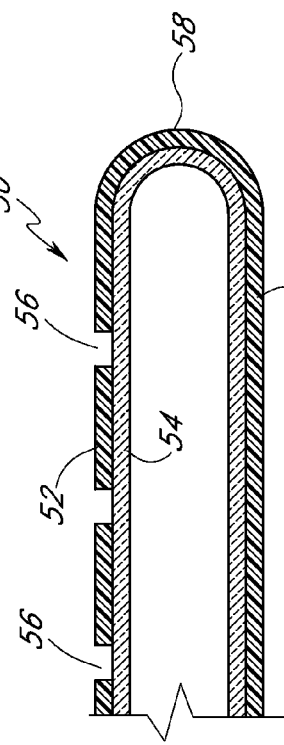
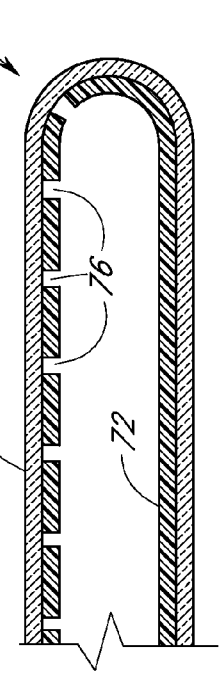

STIMULATING CATHETER

CROSS-REFERENCE TO RELATED APPLICATIONS

This application is related to, and claims the benefit of, U.S. Provisional Patent Application No. 60/941,932, filed Jun. 4, 2007, the entirety of which is hereby incorporated by reference herein and made a part of the present disclosure.

BACKGROUND OF THE INVENTION

1. Technical Field

This invention generally relates to catheters and, in particular, to a catheter that locates the target nerve plexus and delivers fluid medication uniformly across an infusion section of the catheter.

2. Description of the Related Art

Infusion catheters for delivery of fluid medication into anatomical systems, such as the human body, are well known in the art. Such catheters generally include a flexible hollow tube inserted into some region of the anatomy. The tube typically contains one or more axial lumens within which the fluid may flow. The proximal end of the catheter tube can be connected to a fluid source from which fluid can be introduced into the catheter tube. The fluid flows within one of the lumens under pressure supplied at the proximal end of the tube. For each lumen, there are commonly provided one or more exit holes along an infusion section near the distal end of the tube, for fluid to exit the tube. Such exit holes are created by piercing the side wall of the hollow tube.

In certain medical conditions, it can be advantageous to deliver fluid medication to a plurality of sites within a wound area. For instance, some wounds which require pain medication can be in communication with many nerve endings, rather than a single nerve trunk. One example of such a wound is a surgical incision. As stated above, it is known to provide a plurality of exit holes through which the fluid medication exits the catheter tube. The exit holes can be provided at various axial and circumferential positions along the catheter tube in order to control the position of the medication delivery sites. An example of a catheter having this configuration is disclosed in U.S. Pat. No. 5,800,407 to Eldor. Also, in some cases it can be desirable to deliver such medication under low pressure, so that the fluid can be delivered at a relatively low rate. For example, some pain medications must be delivered slowly to avoid toxicity and other side effects. Furthermore, in many cases it is desirable to dispense fluid medication at a substantially uniform rate throughout the infusion section of the catheter, so that the medication is evenly distributed throughout the wound area.

Unfortunately, a limitation of prior art catheters with multiple exit holes, such as the catheter taught by Eldor, is that during low pressure delivery of fluid medication the fluid tends to exit only through the exit hole(s) nearest to the proximal end of the infusion section of the catheter tube. This is because fluids flowing through a tube more readily exit through the exit holes offering the least flow resistance. The longer the flow path followed by the fluid in the lumen, the higher the flow resistance and pressure drop experienced by the fluid. The most proximal holes offer the least flow resistance and pressure drop. Therefore, the fluid tends to exit the catheter tube primarily through these exit holes. As a result, the fluid medication is delivered only to a small region within the wound area. The tendency of the fluid to undesirably flow only through the most proximal exit holes depends upon the hole size, the total number of exit holes, and the flow rate. As the hole size or number of holes increases, the fluid becomes more likely to exit only through the most proximal holes. Conversely, as the flow rate increases, the fluid becomes less likely to do so.

The tendency of the fluid to undesirably exit only through the most proximal holes of the catheter can in some cases be overcome by increasing the flow rate or pressure of the fluid, which causes the fluid to flow through more of the exit holes of the catheter. Indeed, if the flow rate or pressure is sufficiently high, the fluid will flow through all of the exit holes. However, sometimes it is medically desirable to deliver medication at a relatively slow rate, i.e., at a low pressure. Also, even in those cases in which high pressure fluid delivery is acceptable or desirable, prior art catheters do not provide for uniform fluid delivery along the infusion section of the catheter. Rather, the flow rate through the exit holes nearer to the proximal end of the infusion section tends to be greater than that through the exit holes nearer to the distal end. This is because the fluid passing through the more proximal holes experiences a lower flow resistance and pressure drop. In contrast, the fluid flowing through the more distal holes experiences greater flow resistance and pressure drop, and consequently exits at a lower flow rate. The further distal the hole, the lower the exit flow rate of the fluid. As a result, there is an uneven distribution of medication throughout the wound area.

In another known type of infusion catheter, several lumens are provided within a catheter tube. For each lumen, one exit hole is provided by piercing a hole within the wall of the tube. The exit holes are provided at different axial positions along the infusion section of the catheter tube. In this manner, fluid medication may be delivered to several positions within the wound area. While this configuration offers improved fluid distribution, it has some disadvantages. One disadvantage is that the fluid flow rates through the exit holes are not equal, since the more distal exit holes offer a greater flow resistance for the same reasons discussed above. Another disadvantage is that the number of lumens, and consequently the number of fluid exit holes, is limited by the small diameter of the catheter tube. As a result, fluid may be delivered only to a very limited number of positions within the wound area. Yet another disadvantage is that the proximal ends of the lumens must be attached to a complicated manifold which increases the cost of manufacturing the catheter.

An example of a catheter providing a more uniform dispensation of fluid medication throughout an infusion section of the catheter is illustrated by U.S. Pat. No. 5,425,723 to Wang. Wang discloses an infusion catheter including an outer tube, an inner tube concentrically enclosed within the outer tube, and a central lumen within the inner tube. The inner tube has a smaller diameter than the outer tube, so that an annular passageway is formed there between. The outer tube has a plurality of evenly spaced exit holes defining the infusion section of the catheter. In use, fluid flowing within the central lumen passes through strategically positioned side holes within the side walls of the inner tube. In particular, the spacing between adjacent side holes decreases along a length of the inner tube to induce more fluid to pass through the more distal side holes. The fluid then flows longitudinally through the annular passageway before exiting through the exit holes in the outer tube wall. In the annular passageway, the fluid can flow in a distal or proximal direction, depending on the location of the nearest exit hole in the outer tube. This configuration is provided to induce a more uniform exit flow rate of fluid from the catheter.

Unfortunately, the Wang catheter is only effective for relatively high pressure fluid delivery. When used for relatively low pressure fluid delivery, the catheter disclosed by Wang does not provide uniform dispensation of fluid. Instead, the fluid tends to exit through the side holes of the inner and outer tubes that are nearest to the proximal end of the infusion section of the catheter, since these holes offer the least flow resistance. Even for high pressure fluid delivery, there are several limitations of this design. One limitation is that the concentric tubes design is relatively complex and difficult to manufacture. Both tubes must be flexible enough to permit maneuverability through an anatomical system, yet the annular passageway must remain open so that fluid may flow uniformly therein. Another limitation is that the annular passageway can be disturbed if there is a bend in the infusion section of the tube. A bend in the catheter may deform the annular passageway or even cause the inner and outer tubes to come into contact. This can cause an uneven fluid pressure within a longitudinal cross-section of the annular passageway, resulting in non-uniform fluid delivery. Furthermore, it is recognized that a particular class of catheters, such as the Wang catheter, may provide uniform fluid delivery only at high fluid pressure or flow rates. However, there is a need for an infusion catheter belonging to this class that has a relatively simple, easy to manufacture design and can maintain uniform fluid delivery while bent or otherwise physically deformed.

Accurately locating the infusion catheter is a critical step in the administration of anesthetic to the injured area. The nerve plexus is very fragile such that, when damaged by inadvertent and forceful contact by the catheter, is very difficult to repair or reconstruct. For this reason and because the effectiveness of the catheter to deliver nerve blocking medication is dependant on the proximal placement of the catheter, the accurate placement of the infusion catheter adjacent to the nerve is critical. However, accurately positioning the catheter is very difficult with conventional catheter designs not having a means to locate the target nerve plexus integral to the catheter.

Thus, there is a need for an integral infusion catheter for accurately locating the nerve plexus and delivering fluid medication uniformly along its infusion section in a relatively simple, easy to manufacture design which is effective for both high flow rate and low flow rate fluid delivery.

SUMMARY OF SOME EMBODIMENTS

Accordingly, in some embodiments, a catheter is disclosed that is configured to overcome some or all of the limitations described above and that is configured to provide an improved device for delivering fluid medication to a wound area of an anatomical region.

In accordance with an embodiment, a catheter is provided for the uniform delivery of fluid across an anatomical region, comprising an elongated tubular member made of a porous membrane. The membrane can be sized to be inserted through a subcutaneous layer surrounding the anatomical region, such as a person's skin. The membrane can be configured so that a fluid introduced under pressure into an open end of the tubular member will flow through side walls of the tubular member at a substantially uniform rate along a length of the tubular member. Some embodiments also provide a method of uniformly delivering fluid throughout an anatomical region, comprising the steps of inserting the elongated tubular member into the anatomical region and introducing a fluid under pressure into an open end of the tubular member.

Another embodiment of the present disclosure provides a catheter and method for the uniform delivery of fluid throughout an anatomical region. The catheter comprises an elongated support and a porous membrane wrapped around the support. The support can be configured so that one or more lumens are formed between the support and the membrane. Alternatively, the support can be a tubular member having a plurality of holes therein. The method comprises the steps of inserting the above-described catheter into the anatomical region and introducing a fluid under pressure into the proximal end of at least one of the lumens. The fluid can pass through the membrane at a substantially uniform rate into the anatomical region. The present disclosure further provides a method of manufacturing this catheter comprising the steps of forming an elongated support and wrapping a porous membrane around the support so that one or more lumens are formed between the support and the membrane.

Another embodiment of the present disclosure provides a catheter and method for the uniform delivery of fluid throughout an anatomical region. The catheter comprises an elongated tube including a plurality of exit holes along a length thereof and a tubular porous membrane concentrically enclosed within the tube. The tube and membrane define a lumen. The method comprises the steps of inserting the above-mentioned catheter into the anatomical region and introducing a fluid under pressure into the proximal end of the lumen so that the fluid can pass through the membrane and the exit holes at a substantially uniform rate into the anatomical region. The present disclosure further provides a method of manufacturing this catheter, comprising the steps of forming an elongated tube, providing a plurality of exit holes along a length of the tube, forming a tubular porous membrane, and concentrically enclosing the tubular porous membrane within the tube so that the tube and membrane define a lumen.

Another embodiment of the present disclosure provides a device and method for the uniform delivery of fluid throughout an anatomical region. The device can be simple and easy to manufacture, comprising an elongated catheter having a plurality of exit holes along a length thereof. The exit holes may serve as the flow-restricting orifice. Alternatively, a flow-restricting orifice can be provided elsewhere within the catheter or proximal to the catheter. The exit holes may gradually increase in size along the length of the catheter, so that the largest exit hole can be further distal than the smallest exit hole. Alternatively, the holes can be laser drilled and be of approximately the same size. A fluid flowing under pressure within the catheter will preferably flow through substantially all of the exit holes at a substantially equal rate. The method comprises the steps of inserting the catheter into the anatomical region and introducing a fluid under pressure into the proximal end of the catheter. The fluid can flow through the exit holes and enter the anatomical region, preferably flowing through substantially all of the exit holes at a substantially equal rate. The present disclosure further provides a method of manufacturing this device, comprising the steps of forming an elongated catheter and providing a plurality of exit holes along a length of the catheter in a manner so that the exit holes gradually increase in size along the length of the catheter from the proximal end to the distal end thereof.

Another embodiment of the present disclosure provides a catheter and method for delivering fluid medication to an anatomical region. The catheter comprises a tube, a "weeping" tubular coil spring attached to a distal end of the tube, and a stop closing a distal end of the spring. The tube and spring each define a portion of a central lumen. The spring has adjacent coils in contact with one another so that fluid within the spring and below a threshold dispensation pressure can be prevented from exiting the lumen by flowing radially between the coils. The spring has the property of stretching when the fluid pressure is greater than or equal to the threshold dispensation pressure permitting the fluid to be dispensed from the lumen by flowing radially between the coils, i.e. "weeping"

through the spring. Alternatively, the fluid may weep through imperfections in the spring coil. The fluid can be dispensed substantially uniformly throughout the length and circumference of a portion of the spring. In use, fluid can be introduced into an open proximal end of the tube, allowed to flow into the spring, and brought to a pressure greater than or equal to the threshold dispensation pressure so that the fluid weeps through the spring.

Another embodiment of the present disclosure provides a catheter and method for delivering fluid medication to an anatomical region. The catheter comprises a distally closed tube and a "weeping" tubular coil spring, as described above, concentrically enclosed within the tube. A plurality of exit holes can be provided in side walls along a length of the tube, defining an infusion section of the tube. The spring can be enclosed within the infusion section so that a lumen is defined within the tube and spring. In use, fluid can be introduced into a proximal end of the tube, allowed to flow into the spring, and brought to a pressure greater than or equal to the threshold dispensation pressure of the spring so that the fluid can be dispensed from the lumen by weeping through the spring and then flowing through the exit holes of the tube.

Another embodiment of the present disclosure provides a catheter comprising an elongated tube and a solid flexible member positioned within the tube. The tube has a closed distal end and a plurality of exit holes in side walls of the tube. The exit holes are provided along a length of the tube defining an infusion section of the catheter. The tube can be sized to be inserted into an anatomical region. The member can be positioned within the tube and can be sized so that an annular space can be formed between the tube and the member. The member can be formed of a porous material. The catheter can be configured so that a fluid introduced into a proximal end of the tube will flow through the exit holes at a substantially uniform rate throughout the infusion section.

Another embodiment provides a catheter comprising an elongated tube having a plurality of exit slots in side walls of the tube. The slots are provided along a length of the tube defining an infusion section of the catheter. The exit slots are oriented generally parallel to the longitudinal axis of the tube. The tube can be configured so that a fluid flowing therein will flow through substantially all of the exit slots at a substantially equal rate. In one optional aspect, the slots increase in length from the proximal to the distal ends of the infusion section.

Another set of embodiments of the present disclosure provide a catheter comprising an elongated tube, a solid flexible member positioned within the tube, and one or more electrically conductive elements supported by the catheter tube. The conductive elements can be removably connected to a nerve stimulation device that can be peripherally located, such as is described in U.S. Pat. No. 5,830,151, or one that is integral to the catheter, such as is described in U.S. Pat. No. 5,853,373. The disclosures of U.S. Pat. No. 5,830,151 and U.S. Pat. No. 5,853,373 incorporated herein by reference as if fully set forth herein. In either of these configurations, the electrical stimulus (as used herein, stimulus can include, but is not limited to, electrical current, pulses, or signals) from the nerve stimulation device can be transmitted through the catheter lumen to the electrically conductive components.

An electrically conductive ground wire may also be supported by the catheter tube. The ground wire can also be removably attached to the nerve stimulation device. If an electrically conductive ground wire is not included in the catheter, a grounding patch can be positioned externally on the patient's body near to the location of the target nerve. A ground wire can connect the ground patch to the external nerve stimulation device. As discussed in greater detail below, when one or more of the electrically conductive elements are in close proximity with the body's nerves, the electrical stimulus transmitted by the nerve stimulation device through the electrically conductive elements will preferably cause the muscle or muscles associated with the nerve to contract or result in some other response that it is commensurate with the magnitude of electrical stimulation. If the magnitude of the electrical pulse remains constant, the magnitude of the contractions that may be observable may depend on the proximity of the electrically conductive elements relative to the respective nerve such that the magnitude of the muscle contraction or other response will be maximum when the electrically conductive element is in close proximity to the nerve. Additionally, other techniques for using the nerve stimulation device and stimulating catheter of the present disclosure will be readily apparent to those skilled in the art.

Therefore, in this arrangement, the user of the catheter can accurately locate the target nerve with the catheter and/or catheter to that will be embedded into the body's tissue at a position proximate to the target nerve, enabling the user to more accurately position the catheter tube relative to the nerve. Because the contact wire, tip, and tube are integrally formed in the catheter, the user of the catheter can position the tube simultaneous with the step of locating the target nerve as described above. Thus, in some embodiments, the stimulating catheter of the present disclosure can enhance the efficiency and accuracy of the placement procedure. Further, because the electrically conductive elements can be used to transmit the nerve stimulating pulse or signal as opposed to, for example, a sharp, rigid, distal end of a delivery needle, the risk of nerve damage from inadvertent contact by the distal end of the needle can be reduced.

Another set of embodiments of the present disclosure provide an apparatus for the delivery of a fluid to an anatomical region in which the apparatus can comprise a catheter comprising a catheter body, a coiled member, and one or more electrically conductive elements. In some embodiments, the catheter body can comprise a lumen therein, a substantially closed distal end, and an infusion section configured to permit fluid to pass through the catheter body. In some embodiments, the infusion section can define a length that can be less than a length of the catheter body. In some embodiments, the coiled member can be positioned within the lumen of the catheter body and can comprise adjacent coils. The coiled member can define a first end, a second end, and a lumen therethrough. In some embodiments, the second end of the coiled member can be positioned nearer to the distal end of the catheter body than the first end of the coiled member. In some embodiments, the one or more electrically conductive elements can be supported by the catheter body and can be capable of electrical communication with one or more sources of electrical stimulus located peripheral to the catheter body for providing an electrical stimulus to a patient's tissue surrounding the catheter body.

In some embodiments, the coiled member can be configured such that, when the coiled member is in a relaxed position, at least a portion of an outer surface of the adjacent coils can be in contact with one another in at least a portion of the coiled member. Further, the coiled member can have a length that is greater than or equal to the length of the infusion section when the coiled member is in the relaxed position. In some embodiments, the coiled member can be capable of conducting an electrical stimulus, and at least one of the one or more electrically conductive elements can be in communication with the coiled member.

Another set of embodiments of the present disclosure provide a catheter for the delivery of a fluid to an anatomical region. In some embodiments, the catheter can comprise a catheter body having a lumen therein, a substantially closed distal end, and an infusion section configured to permit fluid to pass through the catheter body in a controlled manner. The infusion section can define a length that is less than a length of the catheter body. In some embodiments, the catheter can comprise a first conductive element supported by the catheter body and configured to transmit a first electrical stimulus to an object located external to the catheter body. In some embodiments, the catheter can further comprise a second electrically conductive element supported by the catheter body and configured to transmit a second electrical stimulus to an object located external to the catheter body. In some embodiments, the first and second conductive elements can each be configured to be connectable to a source of electrical stimulus external to the catheter. In some embodiments, the first conductive element can be located on the catheter body at a position that is different than the position of the second conductive element.

In some embodiments, a method for positioning a catheter in a desired anatomical region within a patient's body is provided. In some embodiments, the method can comprise the step of providing a catheter that can comprise a catheter body, a coiled member, and one or more electrically conductive elements. In some embodiments, the catheter body can comprise a lumen therein, a substantially closed distal end, and an infusion section configured to permit fluid to pass through the catheter body. In some embodiments, the infusion section can define a length that is less than a length of the catheter body. In some embodiments, the coiled member can be positioned within the lumen of the catheter body and can comprise adjacent coils. In some embodiments, the coiled member can define a first end, a second end, and a lumen therethrough, wherein the second end of the coiled member can be positioned nearer to the distal end of the catheter body than the first end of the coiled member.

In some embodiments, the one or more electrically conductive elements can be supported by the catheter body for transmitting an electrical stimulus to an object located external to the catheter body. In some embodiments, the coiled member can be configured such that, when the coiled member is in a relaxed position, at least a portion of an outer surface of the adjacent coils can be in contact with one another in at least a portion of the coiled member. In some embodiments, the coiled member can have a length that is greater than or equal to the length of the infusion section when the coiled member is in a relaxed position. In some embodiments, the coiled member can be capable of conducting an electrical stimulus and at least one of the one or more electrically conductive elements can be in communication with the coiled member.

In some embodiments, the method for positioning a catheter in a desired anatomical region within a patient's body can further comprise the steps of positioning the catheter body in the general vicinity of the desired anatomical region, transmitting an electrical stimulus to the tissue surrounding a catheter body through at least one of the one or more electrically conductive elements and observing the response from the patient's body, repositioning the catheter body, if necessary, according to the response that can be observed when the electrical stimulus is applied to the tissue surrounding the catheter body until the catheter body is in the desired location, and delivering a substance through the infusion section of the catheter body.

In some embodiments, another method for positioning a catheter in a desired anatomical region within a patient's body is provided. In some embodiments, the method can comprise the step of providing a catheter that, in some embodiments, can comprise a catheter body comprising a lumen therein, a substantially closed distal end, and an infusion section configured to permit fluid to pass through the catheter body in a controlled manner, the infusion section defining a length that can be less than a length of the catheter body. In some embodiments, the catheter can further comprise a first conductive element supported by the catheter body and configured to transmit a first electrical stimulus to an object located external to the catheter body. In some embodiments, the catheter can further comprise a second electrically conductive element supported by the catheter body and configured to transmit a second electrical stimulus to an object located external to the catheter body. In some embodiments, the first and second conductive elements can each be configured to be connectable to a source of electrical stimulus external to the catheter. In some embodiments, the first conductive element can be located on the catheter body at a position that is different than the position of the second conductive element.

In some embodiments, the method for positioning a catheter in a desired anatomical region within a patient's body can further comprise the steps of positioning the catheter body in the general vicinity of the desired anatomical region, transmitting an electrical stimulus to the tissue surrounding the catheter body through the first conductive element and observing the response from the patient's body, and the step of transmitting an electrical stimulus to the tissue surrounding the catheter body through the second conductive element and observing the response from the patient's body. In some embodiments, the method for positioning a catheter in a desired anatomical region within a patient's body can further comprise the step of comparing the response from the patient's body from the electrical stimulus transmitted through first conductive element to the response from the patient's body from the electrical stimulus transmitted through the second conductive element. In some embodiments, the method for positioning a catheter in a desired anatomical region within a patient's body can further comprise the step of repositioning the catheter body, if necessary, based on the comparison between the response from the patient's body from the electrical stimulus transmitted through first conductive element and the response from the patient's body from the electrical stimulus transmitted through the second conductive element until the catheter body can be in the desired location.

For purposes of summarizing the invention and the advantages achieved over the prior art, certain objects and advantages of the invention have been described herein above. Of course, it is to be understood that not necessarily all such objects or advantages can be achieved in accordance with any particular embodiment of the invention. Thus, for example, those skilled in the art will recognize that the invention can be embodied or carried out in a manner that achieves or optimizes one advantage or group of advantages as taught herein without necessarily achieving other objects or advantages as can be taught or suggested herein.

All of these embodiments are intended to be within the scope of the invention herein disclosed. These and other embodiments of the present disclosure will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Certain embodiments of this invention will now be discussed in detail with reference to the following figures. These figures are provided for illustrative purposes only, and the invention is not limited to the subject matter illustrated in the figures.

FIG. 5 is a side view of another embodiment of a catheter having additional features and advantages.

FIG. 6 is a cross-sectional view of the infusion section of the embodiment of the catheter of FIG. 5 taken along line 6-6 of FIG. 5.

FIG. 7 is a cross-sectional view of another embodiment of a catheter.

FIG. 8 is a side view of another embodiment of a catheter.

DETAILED DESCRIPTION OF THE PREFERRED EMBODIMENTS

Figure 1:
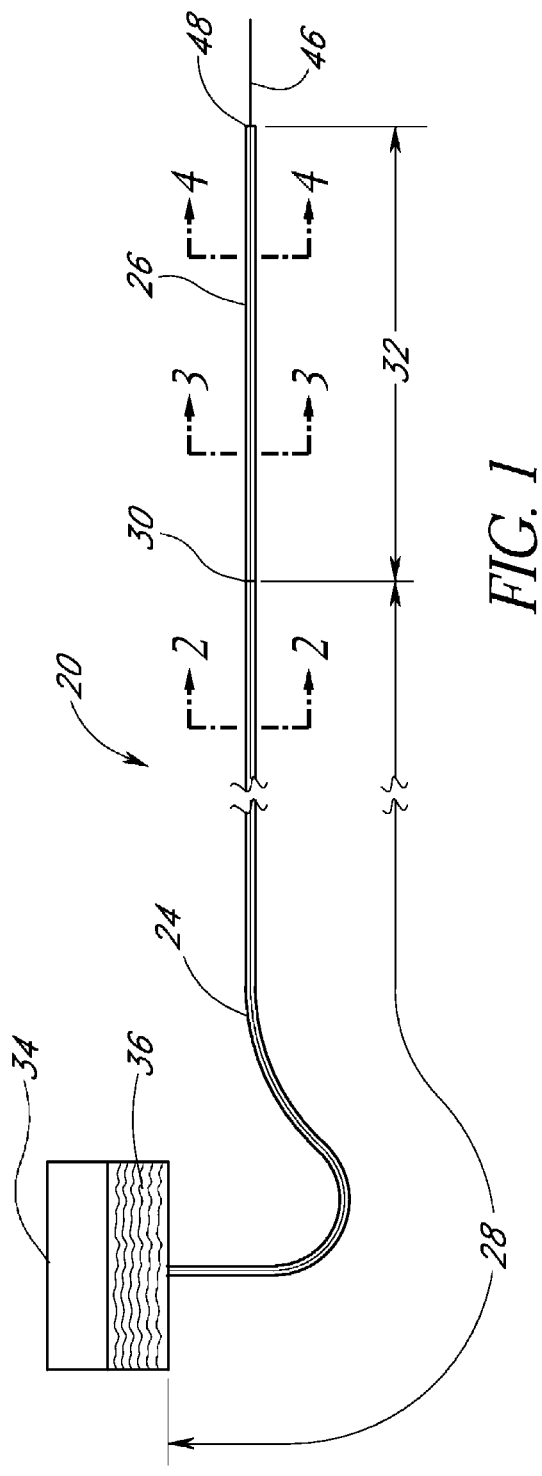
FIG. 1 is a schematic side view of an embodiment of a catheter.

FIGS. 1-4 illustrate an infusion catheter 20 according to one embodiment of the present disclosure. Catheter 20 preferably includes a flexible support 22 (FIGS. 2-4), a non-porous membrane 24, and a porous membrane 26. The membranes 24 and 26 are wrapped around the support 22 to form a plurality of axial lumens between the inner surfaces of the membranes 24 and 26 and the surface of the support 22, as described in greater detail below. The non-porous membrane 24 defines a non-infusing section 28 of the catheter 20, and preferably covers the support 22 from the proximal end thereof to a point 30, shown in FIG. 1. Similarly, the porous membrane 26 defines an infusion section 32 of catheter 20, and preferably covers the support 22 from the point 30 to the distal end of support 22. Alternatively, the catheter 20 can be configured without a non-porous membrane 24. In this configuration, the porous membrane 26 covers the entire length of the support 22, so that the entire length of the support 22 corresponds to the infusion section of the catheter 20. The infusion section can have any desired length. The proximal end of the catheter 20 can be connected to a fluid supply 34 containing a fluid 36 such as a liquid medication. The distal end of catheter 20 may include a cap 48 (FIG. 4) defining the endpoint of the axial lumens within the catheter 20.

In use, the catheter 20 can be inserted into an anatomical system, such as a human body, to deliver fluid medication directly to a wound area within the anatomical system. In particular, the catheter 20 can be designed to deliver medication throughout a generally linear segment of the wound area, corresponding to the infusion section 32 of the catheter 20. Thus, the catheter can be inserted so that the infusion section 32 is positioned within the wound area. By using well known methods, a physician or nurse may insert the catheter 20 with the aid of an axial guide wire 46 positioned within an axial guide wire lumen 44 of the catheter. Once the catheter is positioned as desired, the guide wire 46 is simply pulled back out through the proximal end of the catheter 20. Alternatively, the catheter 20 can be provided without a guide wire or a guide wire lumen.

Figure 3:
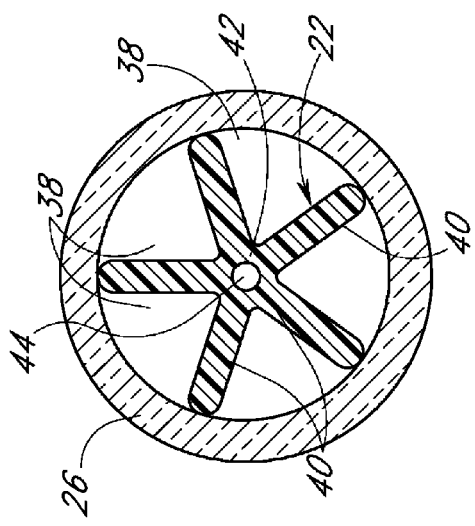
FIG. 3 is a sectional view of the embodiment of the catheter of FIG. 1, taken along line 3-3 of FIG. 1.
Figure 2:
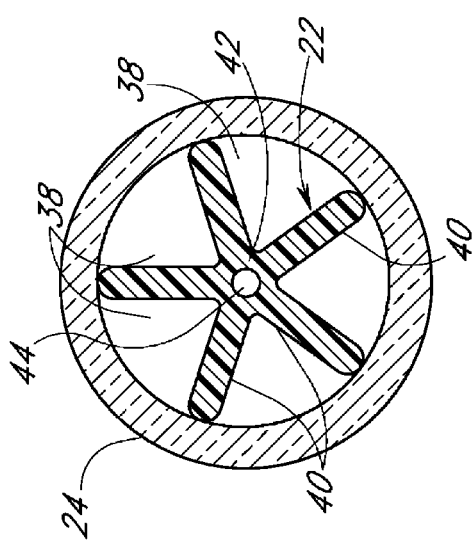
FIG. 2 is a sectional view of the embodiment of the catheter of FIG. 1, taken along line 2-2 of FIG. 1.

FIGS. 2 and 3 illustrate a preferred configuration of the support 22. The surface of the support 22 includes interruptions such as a plurality of ribs 40 as shown in the figures. The interruptions are configured so that when the membranes 24 and 26 are wrapped around the support 22, the membranes form a portion of the walls of a plurality of axial lumens 38 within which the fluid 36 may flow. In a preferred configuration, a plurality of ribs 40 extends radially from a common axial center portion 42 of the support 22. The ribs 40 also extend longitudinally along a length of the support 22, and preferably along the entire length thereof. In the non-infusing section 28, shown in FIG. 2, the non-porous membrane 24 can be tightly wrapped around the outer edges of the ribs 40. As a result, the axial lumens 38 are formed between the inner surface of the non-porous membrane 24 and the outer surface of support 22. Similarly, in the infusion section 32, shown in FIG. 3, the porous membrane 26 can be tightly wrapped around the outer edges of the ribs 40, so that the axial lumens 38 are formed between the inner surface of porous membrane 26 and the outer surface of support 22.

In an alternative embodiment of the catheter 20, the porous membrane 26 can be wrapped around the entire length of the support 20, thus replacing the non-porous membrane 24. In this embodiment, the entire length of the support 22 corresponds to the infusion section 32. According to another alternative embodiment, the support 22 may extend only within the infusion section 32, and a tube can be provided extending from the fluid supply 34 to the proximal end of the support 22. In this embodiment, the tube replaces the non-porous membrane 24 and the portion of the support 22 extending within the non-infusing section 28 of the preferred embodiment. In other words, the tube defines the non-infusing section 28.

In the preferred configuration, the number of ribs 40 equals the number of axial lumens 38. Although five ribs 40 and axial lumens 38 are shown in FIGS. 2 and 3, any suitable number of ribs 40 and lumens 38 can be provided, giving due consideration to the goals of providing a plurality of lumens within the catheter 20, maintaining flexibility, and, if desired, maintaining the fluid independence of the lumens. Herein, the terms "fluid independence," "fluid separation," and the like, when used to describe a plurality of axial lumens, simply mean that the lumens do not fluidly communicate with each other. The membranes 24 and 26 are preferably glued along the outer edges of the ribs 40, utilizing any suitable glue, such as a medical grade glue or epoxy. This prevents the membranes 24 and 26 from slipping, which might occur as the catheter is inserted or removed from the anatomy. More preferably, the membranes are glued along the entire length of the outer edges of each of the ribs 40. Alternatively, the membrane can be wrapped around the support and not secured to the support by a foreign substance. The membrane and support may also be secured to each other by other means known to those of skill in the art. This maintains the fluid independence of the lumens 38. If desired, an axial guide wire lumen 44 can be provided within the axial central portion 42 of the support 22. The guide wire lumen 44 is adapted to receive a guide wire 46 which can be used to aid in the insertion of the catheter 20 into the anatomy, as described above and as will be easily understood by those of skill in the art.

Figure 4:
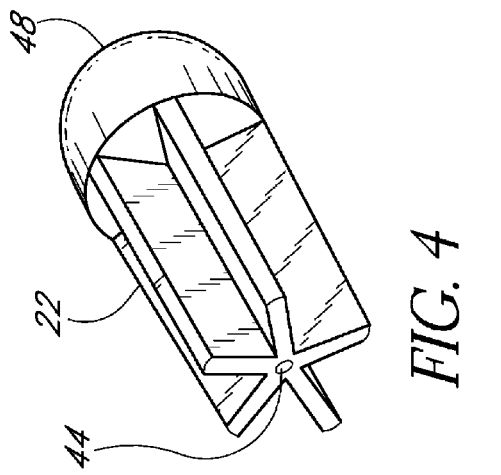
FIG. 4 is a perspective view of the end portion and support beam of the embodiment of the catheter of FIG. 1, illustrating a cross-section taken along line 4-4 of FIG. 1.

As shown in FIG. 4, the catheter 20 preferably includes an end portion or cap 48 secured to the distal end of support 22. End portion 48 can be formed integrally with the support 22 or can be adhesively bonded thereto. Preferably, the proximal end of end portion 48 is circular and has a diameter such that the outer surface of the proximal end of end portion 48 is aligned with the outer edges of the ribs 40 of the support 22, as shown. The porous membrane 26 is wrapped around the proximal end of the end portion 48. The membrane 26 can be glued to the end portion 48 so that fluid 36 within the lumens 38 is prevented from exiting the catheter 20 without passing through the walls of the membrane 26. End portion 48 blocks axial fluid flow through the distal end of catheter 20. However, end portion 48 may optionally be formed from a porous material to permit some axial dispensation of fluid from the distal end of the catheter 20, if desired. The distal end of end portion 48 can be dome-shaped, as shown, to permit the catheter 20 to more easily be inserted into an anatomical region.

The support 22 can be formed from a variety of materials, giving due consideration to the goals of flexibility, lightweight, strength, smoothness, and non-reactivity to anatomical systems, i.e., safety. Suitable materials for the support 22 include nylon, polyamide, teflon, and other materials known to those skilled in the art. The porous membrane 26 can be a sponge-like or foam-like material or a hollow fiber. The membrane 26 can be formed from a variety of suitable materials, giving due consideration to the goals of being flexible and non-reactive to anatomical systems. The membrane 26 preferably has a porosity resulting in substantially uniform dispensation of fluid along the surface area of the infusion section 32 of the catheter 20, and has an average pore size sufficiently small to limit the flow of bacteria through the membrane walls. Some suitable materials for the membrane 26 are polyethylene, polysulfone, polyethersulfone, polypropylene, polyvinylidene difluoride, polycarbonate, nylon, or high density polyethylene. These materials can be biocompatible. The porous membrane 26 may filter out unwanted bacteria from the fluid medication as it passes through the membrane 26. It is known that the smallest bacteria cannot pass through a pore any smaller than 0.23 microns. Thus, the average pore size, or pore diameter, of the porous membrane 26 can be less than 0.23 microns to prevent bacteria from traversing the membrane 26. The average pore size, or pore diameter, of the membrane 26 can be within the range of about 0.1 to 1.2 microns, more preferably within the range of about 0.3 to 1 micron, and even more preferably about 0.8 microns.

As mentioned above, the proximal end of catheter 20 can be connected to a fluid supply 34. The catheter 20 can be configured so that each axial lumen 38 is fluidly independent. In other words, the lumens 38 would not fluidly communicate with one another. The catheter 20 can be connected to a single fluid supply 34, so that the fluid 36 flows within each of the lumens 38. Alternatively, the catheter 20 can be connected to a plurality of separate fluid supplies so that several different fluids may separately flow within the lumens 38. According to this configuration, each lumen 38 can be connected to a separate fluid supply so that the total number of different fluids that can be delivered to the anatomy is equal to the number of lumens 38. Alternatively, the fluid lumens need not be fluidly independent. For example, the membrane 26 may not be secured to the support 22 along the entire length of the support 22, thus permitting fluid 36 to migrate between lumens 38.

In operation, the catheter 20 delivers fluid directly to the area of the anatomy that is adjacent to the infusion section 32. The fluid 36 from the fluid source 34 is introduced into the axial lumens 38 at the proximal end of the catheter 20. The fluid 36 initially flows through the non-infusing section 28. When the fluid 36 first reaches the infusion section 32, it soaks into the porous membrane 26. As more fluid 36 enters the infusion section 32, it diffuses longitudinally within the walls of the membrane 26 until the entire membrane 26 and infusion section 32 are saturated with fluid. At this point the fluid 36 begins to pass through the membrane 26, thereby exiting the catheter 20 and entering the anatomy. Moreover, the fluid 36 can pass through the entire surface area of the porous membrane 26 at a substantially uniform rate, due to the characteristics of the membrane 26. Thus, the fluid is delivered at a substantially equal rate throughout a generally linear segment of the wound area of the anatomy. Furthermore, this advantage is obtained for both low and high pressure fluid delivery.

FIGS. 5 and 6 illustrate a catheter 50 according to an alternative embodiment of the present disclosure. According to this embodiment, the catheter 50 includes an elongated outer tube 52 (also referred to herein as the catheter body) and an inner elongated tubular porous membrane 54. The tubular membrane 54 can be concentrically enclosed within the outer tube 52. More preferably, the tube 52 tightly surrounds and supports the tubular membrane 54 so that a relatively tight fit is achieved between the inner dimensions of tube 52 and the outer dimensions of membrane 54. A plurality of fluid exit holes 56 are provided within the tube 52, preferably throughout the entire circumference thereof. The portion of tube 52 that includes the exit holes 56 defines the infusion section of catheter 50. The tubular membrane 54 need only be provided along the length of the infusion section, but could be longer. Optionally, axial exit holes can be provided within the distal tip 58 of the tube 52. Also, a guide wire and/or guide wire lumen can be provided to aid in the insertion of the catheter 50 into the anatomy, as will be understood by those skilled in the art.

The tube 52 can be formed from any of a variety of suitable materials, such as nylon, polyimide, teflon and other materials known to those skilled in the art, giving due consideration to the goals of non-reactivity to anatomical systems, flexibility, light-weight, strength, smoothness, and safety. In a preferred configuration, the tube 52 can be a 20 gauge catheter tube, having inside and outside diameters of 0.019 inches and 0.031 inches, respectively. The exit holes 56 of tube 52 are preferably about 0.015 inches in diameter and provided at equally spaced axial positions along the tube 52. The holes 56 are preferably arranged so that every hole is angularly displaced about 120° relative to the longitudinal axis of the tube 52, from the angular location of the previous hole. The axial separation between adjacent exit holes 56 can be within the range of about 0.125 to 0.25 inches, and more preferably about 3/16 inch. Also, the infusion section can have any desirable length. This configuration results in a thorough, uniform delivery of fluid throughout a generally linear segment of the wound area. Of course, the exit holes 56 can be provided in any of a variety of alternative arrangements.

The tubular porous membrane 54 can be a sponge-like or foam-like material or a hollow fiber. The tubular membrane 54 may have an average pore size, or pore diameter, less than 0.23 microns to filter bacteria. The pore diameter can be within the range of about 0.1 to 1.2 microns, more preferably within the range of about 0.3 to 1 micron, and even more preferably about 0.8 microns. The tubular membrane 54 can be formed from any of a variety of suitable materials, giving due consideration to the goals of non-reactivity to anatomical systems, maintaining flexibility, fitting within the size constraints of the tube 52, and having a porosity resulting in the substantially uniform dispensation of fluid through all of the exit holes 56 in tube 52. Some suitable materials for the membrane 54 are polyethylene, polysulfone, polyethersulfone, polypropylene, polyvinylidene difluoride, polycarbonate, nylon, or high density polyethylene. Preferable inside and outside diameters of the tubular membrane 54 are 0.010 inches and 0.018 inches, respectively. In the event that a guide wire 46 is provided, the guide wire can be a stainless steel wire about 0.005 inches in diameter. The tube 52 can be secured to the membrane 54 by epoxy or other means known to those skilled in the art. Alternatively, the membrane 54 may contact the tube 52 with an interference fit and not use other materials to secure the membrane 54 in the tube 52.

In operation, the catheter 50 delivers fluid to the region of an anatomical system adjacent to the infusion section of catheter 50. As the fluid flows into the infusion section, it initially soaks into the tubular porous membrane 54. As more fluid enters the infusion section, the fluid diffuses longitudinally within the walls of the tubular member 54. Once the membrane 54 and the tubular space therein are saturated, the fluid passes through the membrane 54 and exits the catheter 50 by flowing through the exit holes 56 of the tube 52. Moreover, the fluid can pass through the membrane substantially uniform throughout the surface area of the membrane 54, resulting in a substantially uniform flow through substantially all of the exit holes 56. Thus, the fluid is delivered at a substantially equal rate throughout the wound area of the anatomy. Furthermore, this advantage is obtained for both low and high pressure fluid delivery.

FIG. 7 illustrates a catheter 70 according to another embodiment of the present disclosure. Catheter 70 includes a tube 72 having a plurality of exit holes 76 in side walls of the tube, and a tubular porous membrane 74 concentrically enclosing the tube 72. Catheter 70 operates in a similar manner to catheter 50 described above in connection with FIGS. 5 and 6. In use, fluid medication passes through the exit holes 76 and then begins to soak into the porous membrane 74. The fluid diffuses longitudinally within the walls of the membrane until the membrane is saturated. Thereafter, the fluid leaves the membrane walls and enters the anatomy. The fluid can be dispensed to the anatomy at a substantially uniform rate throughout the surface area of the membrane 74. As in the previous embodiments, this advantage is obtained for both low and high pressure fluid delivery.

FIG. 8 illustrates a catheter 60 according to another embodiment of the present disclosure. Catheter 60 is better suited for relatively high flow rate delivery of fluid to a region within an anatomical system. Catheter 60 includes a tube 62 having a plurality of exit holes 64 of increasing size. In particular, the more distal exit holes are larger in diameter than the more proximal exit holes. The position of the exit holes 64 on the tube 62 defines the length of the infusion section of the catheter 60. The infusion section can have any desired length. The proximal end of catheter 60 is connected to a fluid supply, and a guide wire and/or guide wire lumen may also be provided for aiding in the insertion of catheter 60 into the anatomy.

As discussed above, for high or low pressure fluid delivery, exit holes near the distal end of a catheter tube generally have increased flow resistance compared to exit holes nearer to the proximal end of the tube. Also, the fluid flowing through the more distal holes experiences a greater pressure drop. Consequently, there is generally a greater flow rate of fluid through the more proximal holes, resulting in non-uniform fluid delivery. In contrast, catheter 60 can provide substantially uniform fluid delivery through substantially all of the exit holes 64, under relatively high flow rate conditions. This is because the larger size of the more distal holes compensates for their increased flow resistance and pressure drop. In other words, since the more distal holes are larger than the more proximal holes, there is a greater flow rate through the more distal holes than there would be if they were the same size as the more proximal holes. The holes 64 can be formed in a gradually increasing size, which can result in substantially uniform fluid delivery. In addition, the exit holes 64 can be sized so that they combine to form a flow-restricting orifice, as described below in connection with the embodiment of FIG. 12.

As compared to prior art catheters, catheter 60 can be simple and easy to manufacture. All that is required is to drill a plurality of exit holes 64 in the tube 62. Furthermore, catheter 60 can sustain greater bending than prior art catheters while maintaining operability. In contrast to prior art catheters, such as the Wang catheter, if the tube 62 is bent somewhat, it will still deliver fluid relatively uniformly. This is because the tube 62 has a single lumen with a relatively large cross-section. When the tube 62 is somewhat bent, fluid flowing within the lumen is less likely to experience blockage and a consequent pressure change which might lead to non-uniform fluid dispensation.

The tube 62 of catheter 60 can be formed from any of a wide variety of materials, giving due consideration to the goals of non-reactivity to anatomical systems, flexibility, light-weight, strength, smoothness, and safety. Suitable materials include nylon, polyimide, teflon, and other materials known to those skilled in the art. The infusion section can have any desired length but can be about 0.5 to 20 inches long, and more preferably about 10 inches long. The diameter of the exit holes 64 preferably ranges from about 0.0002 inches at the proximal end of the infusion section to about 0.01 inches at the distal end thereof. The largest, i.e., most distal, exit hole 64 can be about 0.25 inches from the distal end of the tube 62. In the preferred configuration, the axial separation between adjacent holes 64 is within the range of about 0.125 to 0.25 inches, and more preferably about 3/16 inch. Optionally, the holes 64 can be provided so that adjacent holes are angularly displaced by about 120° as in the embodiment of FIG. 5. Of course, if too many exit holes 64 are provided, the tube 62 can be undesirably weakened.

Figure 9:
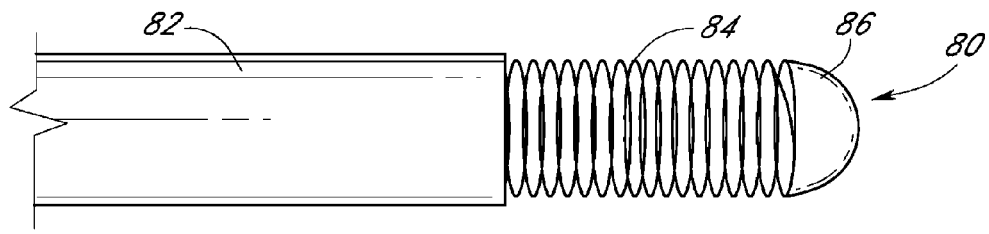
FIG. 9 is a side view of another embodiment of a catheter.
Figure 10A:
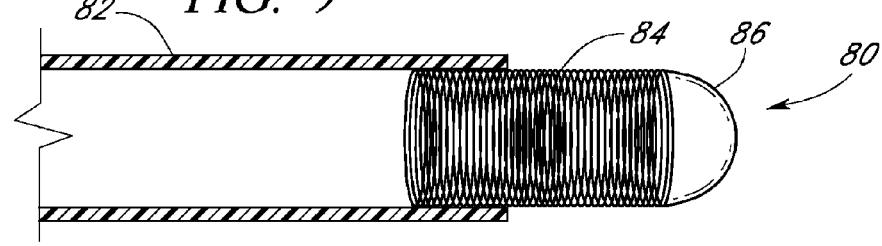
FIG. 10A is a cross-sectional view of the embodiment of the catheter of FIG. 9, illustrating an unstretched state of the spring.
Figure 10B:
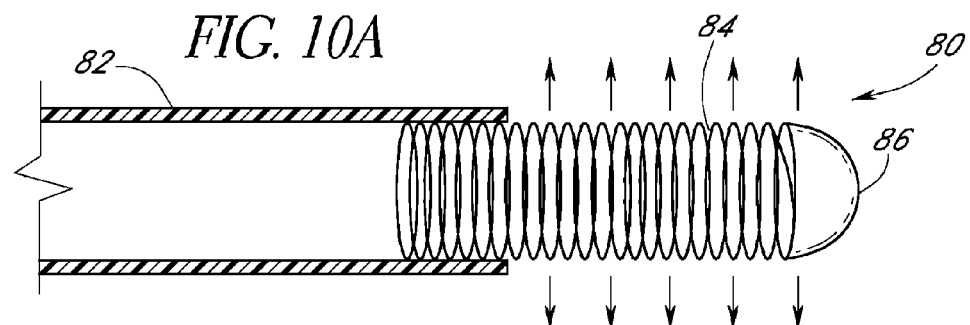
FIG. 10B is a cross-sectional view of the embodiment of the catheter of FIG. 9, illustrating a stretched state of the spring.

FIGS. 9, 10A, and 10B illustrate a catheter 80 according to another embodiment of the present disclosure. The catheter 80 comprises a tube 82, a "weeping" tubular coil spring 84, and a stop 86. The proximal end of the spring 84 is attached to the distal end of the tube 82 so that the tube and spring each define a portion of a central lumen. A preferably dome-shaped stop 86 is attached to and closes the distal end of the spring 84. The portion of the spring 84 that is distal to the tube 82 comprises the infusion section of the catheter 80. In an unstretched state, shown in FIG. 10A, the spring 84 has adjacent coils in contact with one another so that fluid within the spring and below a threshold dispensation pressure is prevented from exiting the lumen by flowing radially between the coils. The spring 84 has the property of stretching longitudinally, as shown in FIG. 10B, when the fluid pressure is greater than or equal to the threshold dispensation pressure of the spring, thereby permitting the fluid to be dispensed from the lumen by "weeping," i.e., leaking radially outward between the coils. Alternatively, the spring may stretch radially without elongating to permit fluid to weep through the coils of the spring. Further, the spring may stretch both longitudinally and radially to permit weeping, as will be understood by those of skill in the art. The fluid between the coils of the spring can be dispensed substantially uniformly throughout the length and circumference of the portion of the spring that is distal to the tube 82, i.e., the infusion section. The catheter 80 can be used for both high or low flow rate fluid delivery.

In use, the catheter 80 is inserted into an anatomical region so that the spring 84 is in a region to which fluid medication is desired to be delivered. The spring is initially in an unstretched state, as shown in FIG. 10A. The fluid is introduced into a proximal end of the tube 82 of the catheter 80 and flows into and through the spring 84 until it reaches the stop 86. As fluid is continually introduced into the proximal end of the tube 82, the fluid builds inside of the spring 84. When the spring 84 is filled with fluid, the fluid pressure rises more quickly. The fluid imparts a force directed radially outward onto the spring coils. As the pressure builds, the outward force becomes larger. Once the fluid pressure rises to the threshold dispensation pressure, the outward force causes the spring coils to separate slightly so that the spring stretches longitudinally, as shown in FIG. 10B. Alternatively, the coils may separate radially, as discussed above. The fluid then flows through the separated coils to be dispensed from the catheter 80. Moreover, the dispensation can be uniform throughout the infusion section of the catheter 80. As fluid is continually introduced into the tube 82, the spring 84 remains stretched to continually dispense fluid to the desired region within the anatomy. If the fluid introduction temporarily ceases, the fluid pressure within the spring 84 may fall below the threshold dispensation pressure. If so, the spring will compress so that the coils are once again adjacent and the fluid is no longer dispensed.

Several spring types will achieve the purposes of this invention. Suitable spring types are 316L or 402L, which can be readily purchased. In a preferred configuration, the spring 84 has about 200 coils per inch along its length. In this configuration, the spring can sustain a high degree of bending without leaking fluid from within, and only a severe bend will cause adjacent coils to separate. Thus, the spring 84 can be flexed considerably within an anatomical region without causing fluid to leak and therefore be dispensed to only one region within the anatomy. The spring 84 can have any desired length to define the length of the infusion section of the catheter 80. The spring can be formed from a variety of materials, giving due consideration to the goals of strength, flexibility, and safety. A preferred material is stainless steel. In the preferred configuration, the inside and outside diameters of the spring are about 0.02 inches and 0.03 inches, respectively, and the spring wire has a diameter of about 0.005 inches. The proximal end of the spring 84 can be concentrically enclosed within the distal end of the tube 82. The spring can be glued to the inside wall of the tube 82 using, for example, a U.V. adhesive, a potting material, or other bonding materials. Alternatively, the spring can be soldered within the tube 82 or be fitted with a proximal plug and tightly plugged into the tube 82.

The tube 82 and stop 86 can be formed from any of a variety of materials, giving due consideration to the goals of flexibility, light-weight, strength, smoothness, and safety. Suitable materials include nylon, polyimide, teflon, and other materials known to those skilled in the art.

Figure 11:
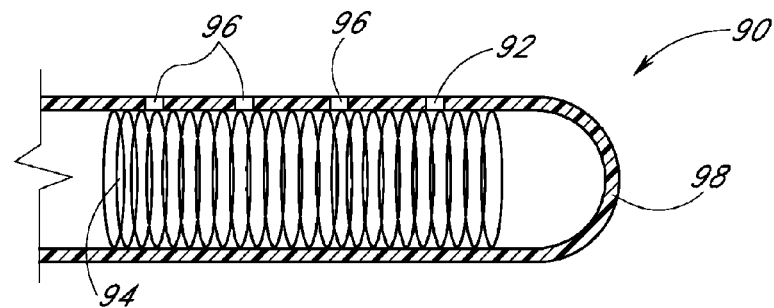
FIG. 11 is a cross-sectional view of another embodiment of a catheter.

FIG. 11 illustrates a catheter 90 according to another embodiment of the present disclosure. The catheter 90 comprises a distally closed tube 92 and a "weeping" tubular coil spring 94 concentrically enclosed within the tube 92 so that a lumen is defined within the tube and spring. A plurality of exit holes 96 are provided along a length of the tube 92, in the side wall thereof. The length of the tube 92 including such exit holes 96 defines an infusion section of the catheter 90. The exit holes 96 are preferably provided throughout the walls of the infusion section. The infusion section can have any desired length. In the preferred configuration, the axial spacing between adjacent holes 96 is within the range of about 0.125 to 0.25 inches, and more preferably about 3/16 inch. Adjacent holes 96 are preferably angularly spaced apart by about 120°. The spring 94 can be enclosed within the infusion section of the catheter and configured similarly to the spring 84 of the embodiment of FIGS. 9, 10A and 10B. The spring 94 can be longer than the infusion portion and positioned so that all of the exit holes 96 are adjacent to the spring 94. In this configuration, the fluid is prevented from exiting the lumen without flowing between the spring coils. A stop can be attached to the tube to close the distal end thereof. Alternatively, the tube 92 can be formed with a closed distal end. The catheter 90 can be used for high or low flow rate fluid delivery.

In use, the catheter 90 is inserted into an anatomical region so that the infusion section is in a region to which fluid medication is desired to be delivered. The fluid is introduced into a proximal end of the tube 92 of the catheter 90 and flows through the spring 94 until it reaches the closed distal end of the tube 92. As fluid is continually introduced into the proximal end of the tube 92, the fluid builds inside of the spring 94. Eventually, the spring 94 becomes filled with fluid, the fluid pressure rises, and the fluid weeps through the spring coils as described above in connection with the embodiment of FIGS. 9, 10A, and 10B. Moreover, the fluid flows through the spring coils substantially uniformly throughout the length and circumference of the spring 94. The fluid then exits the tube 92 by flowing through the exit holes 96 of the infusion section. The exit holes can be equal in size so that the fluid flows at a substantially equal rate through the exit holes, which can result in a generally uniform distribution of fluid throughout a desired region of the anatomy. As fluid is continually introduced into the catheter 90, the spring 94 remains stretched to continually dispense fluid from the catheter. If the fluid introduction ceases temporarily, the fluid pressure within the spring 94 may fall below the threshold dispensation pressure. If so, the spring may compress so that the coils are once again adjacent and the fluid is no longer dispensed.

In the preferred configuration, the spring 94 and tube 92 are in contact along the entire length of the spring, so that the fluid weeping through the spring is forced to flow through the holes 96 of the infusion section. Preferably, one end of the spring 94 is attached to the inside walls of the tube 92, permitting the other end of the spring to be displaced as the spring stretches. The spring can be glued to the tube 92 with, for example, a U.V. adhesive, potting material, or other bonding materials. Alternatively, an end of the spring can be soldered onto the inner walls of the tube 92. The tube 92 can be formed from any suitable material. The inside walls of the tube 92 are preferably smooth so that the spring can more freely stretch and compress.

Figure 12:
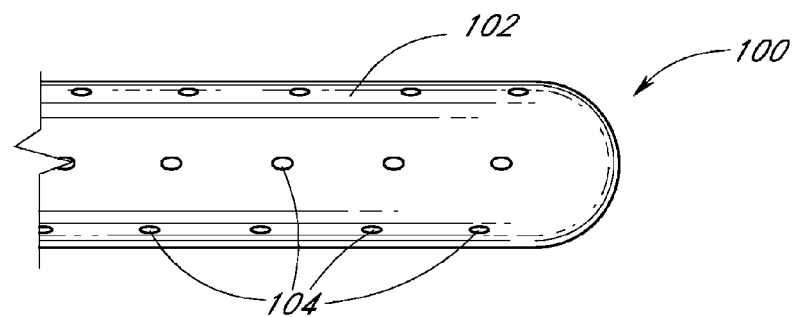
FIG. 12 is a side view of another embodiment of a catheter.

FIG. 12 illustrates a catheter 100 according to another embodiment of the present disclosure. The catheter 100 comprises a distally closed tube 102 having a plurality of exit holes 104 in side walls of the tube 102. The portion of the tube 102 having exit holes 104 defines an infusion section of the catheter 100. The exit holes 104 are sized to have a combined area of opening that is smaller than the area of any other flow-restricting cross-section or orifice of the catheter. Thus, the exit holes 104 are the flow-restrictor of the catheter 100. In use, the catheter can dispense fluid through substantially all of the exit holes 104. A fluid introduced into a proximal end of the tube 102 flows through the tube until it reaches the closed distal end thereof. At this point, the fluid builds within the infusion portion of the catheter. The fluid is substantially prevented from flowing through the holes 104, due to their small size. Eventually, the infusion portion of the catheter becomes filled with fluid. As fluid is continually introduced into the proximal end of the tube 102, the fluid pressure begins to build. At some point the pressure becomes sufficiently high to force the fluid through the exit holes 104. Moreover, the fluid flows through substantially all of the exit holes 104.

In this preferred configuration, the exit holes 104 are all equal in size so that the fluid is dispensed at a substantially equal rate through substantially all of the holes. The holes 104 are preferably laser drilled to achieve a very small hole diameter. A preferred diameter of the exit holes 104 is about 0.0002 inches, or about 5 microns. Numerous exit holes 104 can be provided within the tube 102. The holes can be formed throughout the circumference of the infusion portion of the catheter 100, to more uniformly deliver the fluid throughout an anatomical region. A preferred axial spacing between adjacent holes 104 is within the range of about 0.125 to 0.25 inches, and more preferably about 3/16 inch. The catheter 100 can be used for high or low flow rate fluid delivery. The tube 102 can be formed from any of a variety of materials known to those skilled in the art and discussed previously.

Figure 13:
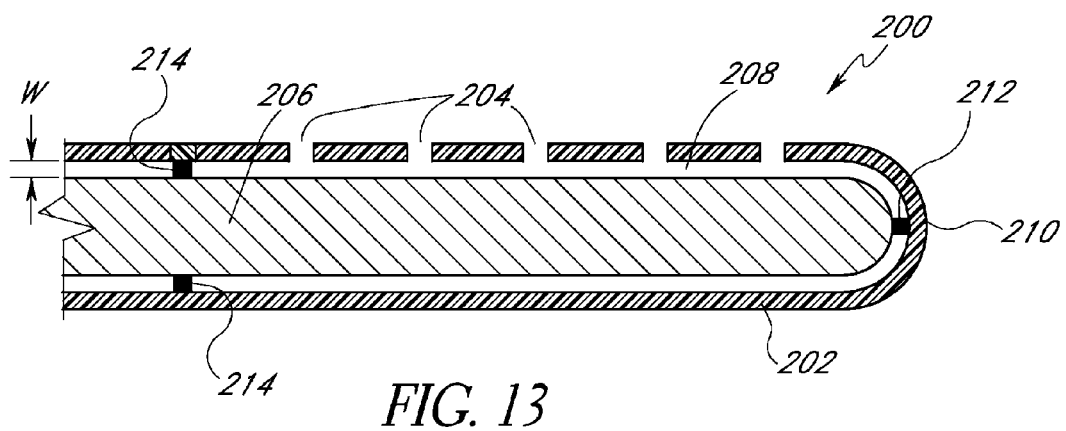
FIG. 13 is a longitudinal cross-sectional view of another embodiment of a catheter.

FIG. 13 illustrates a catheter 200 according to another embodiment of the present disclosure. Catheter 200 includes a distally closed tube 202 having a plurality of exit holes 204 therein along an infusion section of the catheter, as in the above-described embodiments. The holes 204 are desirably provided throughout the circumference of the tube 202. Enclosed within the tube 202 is an elongated member 206 formed of a porous material. Preferably, the member 206 is generally cylindrical in shape, and solid. Preferably, the member 206 is positioned within the tube 204 so that an annular space 208 is formed between the outer surface of the member 206 and the inner surface of the tube 202. Preferably, the member 206 extends from the distal end 210 of the tube 202 rearwardly to a point proximal of the infusion section of the catheter. Alternatively, the member 206 may extend along only a portion of the infusion section. In some embodiments, the member 206 can be generally concentric with the tube 202. However, in some embodiments, non-concentric designs will achieve the advantages of the invention. Preferably, the member 206 is manufactured of a flexible material to assist with the placement of the catheter 200 in the body of a patient.

In operation, fluid medication flowing in the tube 202 saturates the porous member 206 and flows into the annular region 208. Once the member 206 is saturated, the fluid in the member 206 flows into the region 208 and out of the catheter 200 through the exit holes 204. Because the fluid pressure can be uniform throughout the annular region 208, the fluid can flow substantially uniformly through all of the holes 204. There are several advantages of the annular region 208. One advantage is that it tends to optimize the uniformity of flow through the exit holes 204. Also, the member 206 can be formed from a porous material that tends to expand when saturated with liquid. If so, the member 206 preferably expands into the annular region 208 without pressing against the tube 202. This limits the possibility of high pressure regions at the interior surface of the tube 202, which could cause uneven exit flow of the medication within the wound site. Alternatively, the member 206 may expand and come into contact with the tube 202, and still accomplish the goals of the present disclosure.

The member 206 is formed of a porous material having an average pore size preferably within the range of 0.1-50 microns, and more preferably about 0.45 microns. The radial width W of the annular region 208 can be within the range of 0 to about 0.005 microns, and more preferably about 0.003 microns. The member 206 can be formed of any of a variety of materials, giving due consideration to the goals of porosity, flexibility, strength, and durability. A preferred material is Mentek.

Figure 14:
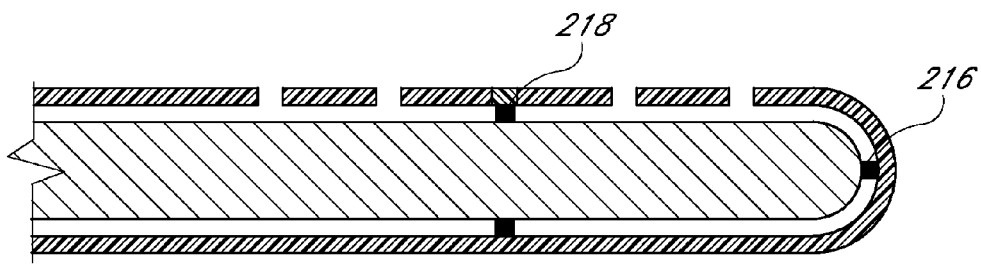
FIGS. 14-16 are longitudinal cross-sectional views of additional embodiments of catheters similar to the embodiment illustrated in FIG. 13, illustrating alternative attachments between the internal porous member and the tube.
Figure 15:
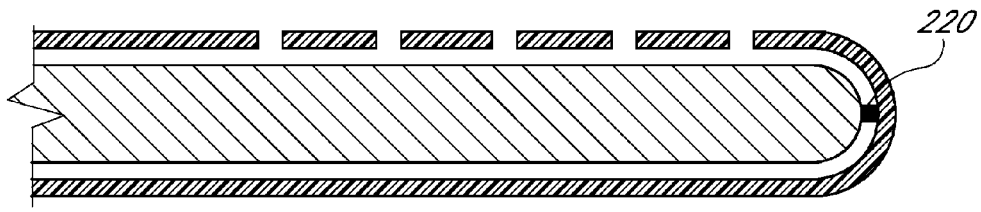
Figure 16:
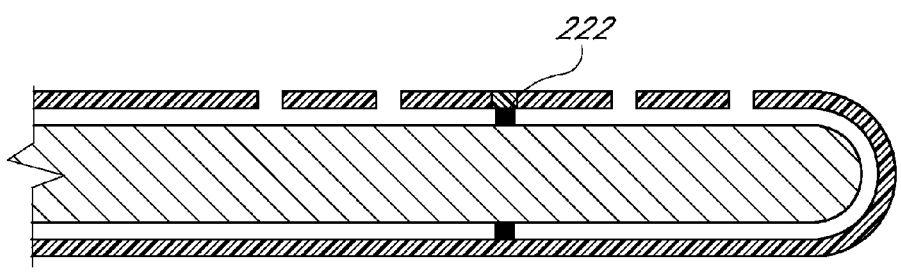

The member 206 can be secured within the tube 202 by the use of an adhesive. In one embodiment, as shown in FIG. 13, the adhesive is applied at the distal end of the member 206 to form a bond with the interior surface of the distal end of the tube 202. Preferably, adhesive is applied at or near the proximal end of the infusion section of the catheter 200. Additionally, the adhesive can be applied to the circumference of the member 206 at any longitudinal position thereof, forming a ring-shaped bond with the interior surface of the tube 202. For example, in the embodiment of FIG. 13, a ring-shaped bond 214 is provided just proximal of the infusion section of the catheter 200. Other configurations are possible. For example, FIG. 14 shows an embodiment in which the adhesive is applied to the distal end of the member 206 to form a bond 216, and also at generally the center of the infusion section to form a ring-shaped bond 218. FIG. 15 shows an embodiment in which the adhesive is applied only to the distal end of the member 206 to form a bond 220. FIG. 16 shows an embodiment in which the adhesive is applied only to the center of the infusion section to form a ring-shaped bond 222. Those of ordinary skill in the art will understand from the teachings herein that the adhesive can be applied in any of a variety of configurations. Thus, for example, adhesive at the distal end of the catheter (i.e., 212, 216, and 220 in FIGS. 13, 14, and 15, respectively) is not required.

In the current best mode of the invention, preferably two bonds are incorporated—one at the most proximal hole and one at the most distal hole of the catheter. Each bond is formed with an adhesive as described below.

The ring-shaped bond 214 can be formed by pouring the adhesive in liquid form through one of the exit holes 204 when the member 206 is in the tube 202. The adhesive, having a generally high viscosity, tends to flow about the circumference of the member 206, rather than into the body of the member. The adhesive thus forms a ring-shaped bond with the tube 202, as will be understood by those of skill in the art. Also, the adhesive plugs the exit hole 204 through which it is poured. Any of a variety of different types of adhesives will be acceptable, a preferred adhesive being Loctite.

Figure 17:
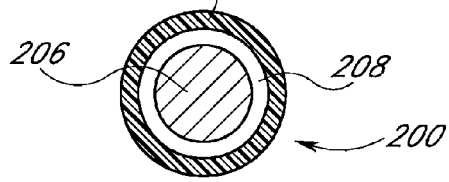
FIG. 17 is a transverse cross-sectional view of the embodiments of the catheters illustrated in FIGS. 13-16, wherein the internal porous member is generally concentric with the outer tube.
Figure 18:
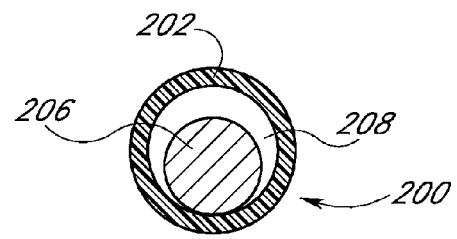
FIG. 18 is a transverse cross-sectional view of the embodiments of the catheters illustrated in FIGS. 13-16, wherein the internal porous member is generally not concentric with the outer tube.

As mentioned above, the member 206 can be concentric with the tube 202. FIG. 17 shows a cross-section of a catheter 200 in which the member 206 is concentrically enclosed within the tube 202. Alternatively, the member 206 can be positioned adjacent to the tube 202, as shown in FIG. 18. The configuration of FIG. 18 can be easier to manufacture than that of FIG. 17, since the member 206 does not have to be centered within the tube 202.

Those of ordinary skill in the art will understand from the teachings herein that the member 206 can be of any desired length and can extend along any desired length of the infusion section of the catheter 200. For example, the member 206 does not have to extend to the distal end of the tube 202. Further, the proximal end of the member 206 can be either distal or proximal to the proximal end of the infusion section.

Figure 19:
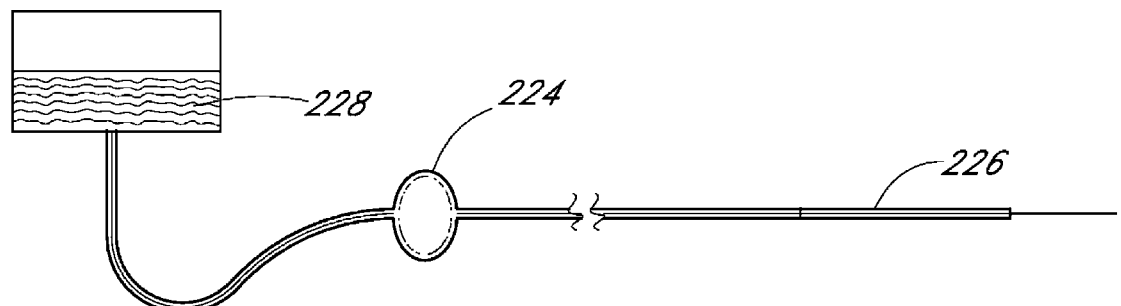
FIG. 19 is a schematic illustration of an embodiment of a catheter used in conjunction with an air eliminating filter.

When any of the catheters of the above embodiments is used, the catheter may initially have air inside of the catheter tube. For example, the catheter 200 shown in FIG. 13 may have air inside of the porous material of the member 206. The introduction of liquid medication into the catheter forces the air to flow out of the exit holes. However, this may take several hours. If the catheter is inserted into a patient while air is inside, and liquid medication is introduced into the catheter, the patient's wound site may receive little or no medication until air is expelled from the catheter tube. Thus, it is preferred to run the liquid medication through the catheter prior to inserting the catheter into a patient, to ensure that the air is expelled from the catheter prior to use. Further, with reference to FIG. 19, an air filter 224, as known in the art, can be inserted into the catheter tubing proximal the infusion section 226 of the catheter 200. The filter 224 prevents undesirable air from entering the infusion section 226 of the catheter 200.

Figure 20:
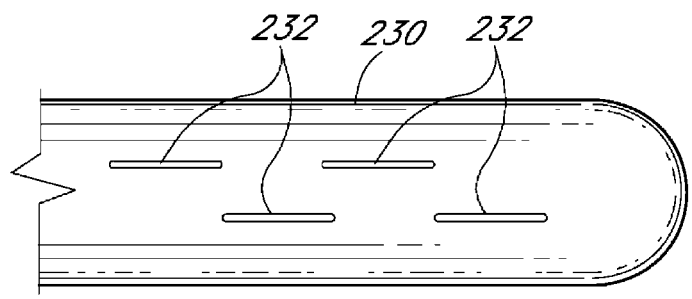
FIG. 20 is a side view of another embodiment of a catheter.
Figure 21:
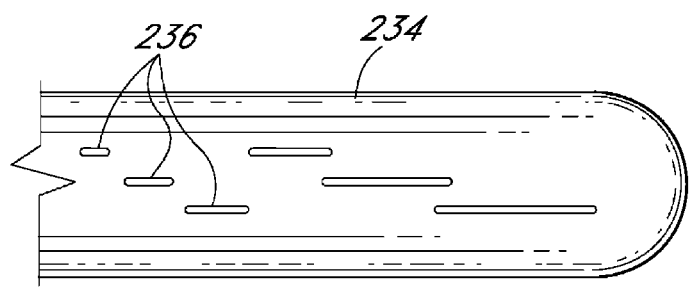
FIG. 21 is a side view of another embodiment of a catheter.

FIGS. 20 and 21 illustrate catheter tubes having elongated exit holes or slots. These catheter tubes can be used in place of the catheter tubes shown and described above. FIG. 20 shows a tube 230 having exit holes or slots 232 that are elongated in the longitudinal direction of the tube 230. The slots 232 are preferably provided throughout the circumference of the tube 230, along the infusion section of the catheter. Compared to smaller exit holes, the elongated slots 232 tend to increase the flow rate of fluid exiting the catheter, by reducing the flow impedance experienced by the fluid. Preferably, the slots 232 can be oriented longitudinally on the catheter body so as not to compromise the structural integrity of the catheter 200, as will be easily understood by those of skill in the art.

FIG. 21 shows a tube 234 having exit holes or slots 236 whose lengths increase along the length of the tube in the distal direction. In the illustrated embodiment, the slots nearer to the proximal end of the infusion section of the tube 234 are shorter in length than the slots nearer to the distal end of the infusion section. As in the embodiment of FIG. 8, the catheter tube 234 can provide substantially uniform fluid delivery through substantially all of the exit slots 236, under relatively high flow rate conditions. This is because the larger size of the more distal slots compensates for their increased flow resistance and pressure drop. In other words, since the more distal slots are larger than the more proximal slots, there is a greater flow rate through the more distal slots than there would be if they were the same size as the more proximal slots. The slots 236 can be provided in a gradually increasing length, which results in substantially uniform fluid delivery. Further, the elongated slots result in generally higher exit flow rates, as in the embodiment of FIG. 20.

A stop can be attached to the tube to close the distal end thereof. Alternatively, the tube 302 can be formed with a closed distal end. The catheter 300 can be used for high or low flow rate fluid delivery.

FIGS. 22-28 show several embodiments of catheters of the present disclosure having electrically conductive elements (such as, but not limited to, conductive wires or bands) supported by the catheter body that can communicate with a peripheral nerve stimulation device (not shown) for locating a target nerve to facilitate positioning the infusion catheter. In some embodiments, the electrically conductive elements can be formed integrally with a catheter body. The nerve stimulation device used for the embodiments illustrated in FIGS. 22-26 can be of the kind typically used in the field, such as the apparatus described in U.S. Pat. No. 5,830,151, which is incorporated herein by reference as if set forth fully herein. Further, the electrically conductive elements of any of the embodiments illustrated in FIGS. 22-26 can be used with any of the catheter embodiments described above.

Figure 22:
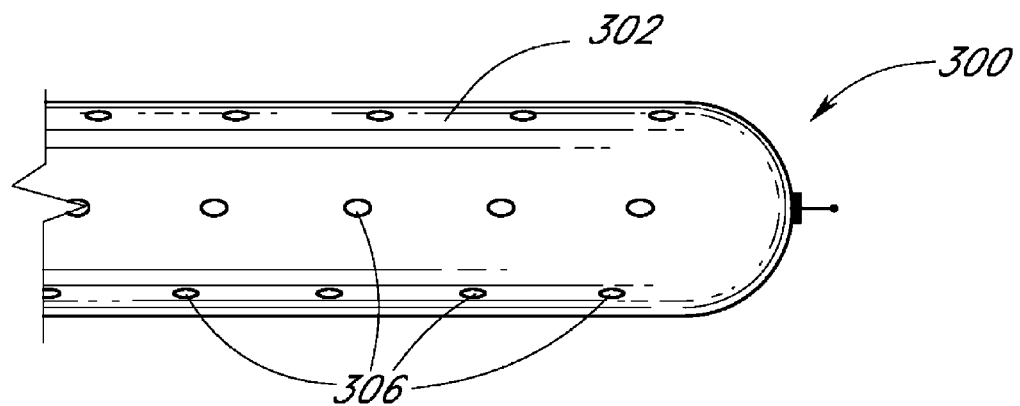
FIG. 22 is a side view of another embodiment of a catheter.
Figure 23:
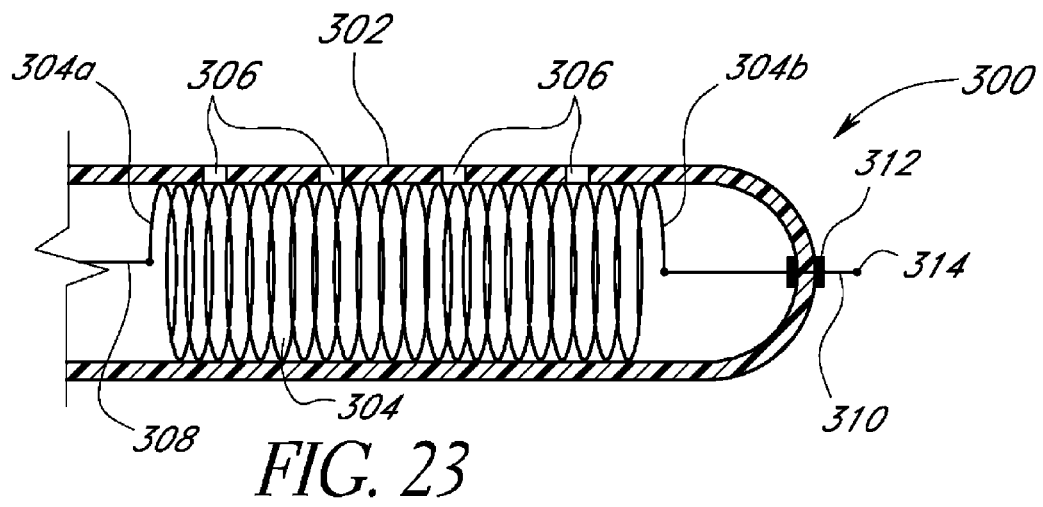
FIG. 23 is a cross-sectional view of the embodiment of the catheter illustrated in FIG. 22.

FIGS. 22 and 23 illustrate a catheter 300 comprising a tube 302 and a coiled member, such as a "weeping" tubular coil spring 304 concentrically enclosed within the tube 302 so that a lumen is defined within the tube and spring. The catheter 300 can be configured similar to the catheter 90 illustrated in FIG. 11 above. As such, a plurality of exit holes 306 is provided along a length of the tube 302, in the side wall thereof. The length of the tube 302 including such exit holes 306 defines an infusion section of the catheter 300. The exit holes 306 are preferably provided throughout the walls of the infusion section. The infusion section can have any desired length. The spring 304 can be enclosed within the infusion section of the catheter 300 and configured similarly to the spring 84 of the embodiment of FIGS. 9, 10A and 10B. The spring 304 (in a relaxed state) can be longer than the infusion portion and positioned so that all of the exit holes 306 are adjacent to the spring 304. In this configuration, the fluid can be substantially prevented from exiting the lumen without flowing between the spring coils. Thus, the tube 302 and spring 304 in the arrangement illustrated in FIGS. 22-23 are configured similar to the tube 98 and spring 94 of the catheter 90 illustrated in FIG. 11. However, the tube 302 and catheter 300 can be configured in any manner described above or otherwise to uniformly diffuse a fluid to a desired area. The fluid could be a medication, such as an anesthetic.

In the arrangement illustrated in FIGS. 22 and 23, the catheter 300 has an electrically conductive lead wire 308 that can be attached to the proximal end 304a of an electrically conductive spring 304. The lead wire 308 passes through the catheter lumen of the type described above and removably attaches to a preferably peripherally located nerve stimulation device by use of an alligator clip or other similarly configured connection device. A contact wire 310 can be attached to the distal end 304b of the spring 304 and passes through a sealed, or substantially sealed, opening 312 located at the center portion of the distal end of the tube 302. A distinct seal member may be utilized or the opening 312 can be sized such that it tightly surrounds the wire 310 without any additional seal elements, among other possible sealing mechanisms. Note that the contact wire 310 can be formed integrally with and, hence, embedded into, the tube 302 such that there would be no opening at the end of the tube 302 that would require a seal. In some embodiments, the spring 304 can help stabilize the position of the contact wire 310 relative to the opening 312. Because the spring 304 can be electrically conductive, the electric pulse fed to the proximal end 304a of the spring by the nerve stimulation device through the lead wire 308 can be transmitted to the contact wire 310.

The spring 304, lead wire 308, and contact wire 310 can be integrally formed from a single piece of electrically conductive wire. The tube 302 can be made of an electrically insulating material so that the electrical pulse transmitted through the lead wire 308, spring 304, and contact wire 310 does not transfer to any tissue of the body adjacent to the tube 302, except through the contact wire 310. The contact wire 310 can be coated with an insulating material at all points along the length of the contact wire 310 except for the tip 314 of the contact wire 310 to prevent leakage of the electrical pulse into body tissue located adjacent to the contact wire 310. An electrically conductive ground wire may also protrude from the distal end of the catheter tube to provide a ground in the body for the nerve stimulation device. In the arrangement illustrated in FIGS. 22 and 23, the catheter 300 does not have a ground wire protruding therefrom. In this arrangement, a grounding device, such as a grounding patch (not shown), would preferably be positioned externally on the patient's body near to the location of the target nerve. A ground wire connects the ground patch to the external nerve stimulation device. The ground wire would also be preferably removably attached to the nerve stimulation device. After the tube is positioned in the desired location, the nerve stimulation device can be disconnected from the lead wire 308.

So configured, electrical stimulus can be transmitted from a peripheral nerve stimulation device to the tip 314 of the contact wire 310 that can be positioned within the catheter tube 302. The peripheral nerve stimulation device preferably sends intermittent electrical stimulus through the lead wire 308, spring 304, and contact wire 310 to the electrically conductive tip 314. The electrical pulse can be transmitted through the tip 314 into the tissue of the body, or nerve, to which it contacts or within close proximity to. The grounding patch or grounding wire described above completes the electrical circuit for the nerve stimulation device. By electrically stimulating the nerves associated with respective muscles of the body through the nerve stimulation device, the muscles associated to the nerves will contract in response to the electrical pulse supplied by the nerve stimulation device when the tip 314 is positioned in contact with or proximal to the nerve. The magnitude of the muscle twitch or contraction depends on the voltage of the electrical pulse and also the proximity of the tip 314 to the nerve. Therefore, if a constant voltage is applied, the user of the device described herein can detect the distance of the tip 314 to the target nerve by the magnitude of the muscle contractions that result from the electrical pulse. After the catheter 300 is positioned in the desired location, the tip 314 and contact wire 310 can be retracted by retracting the lead wire 308 back through the lumen far enough such that the tip 314 is either adjacent to or inside of the sealed opening 312 and, also, such that all of the exit holes 306 remain positioned adjacent to the spring 304.

Figure 24:
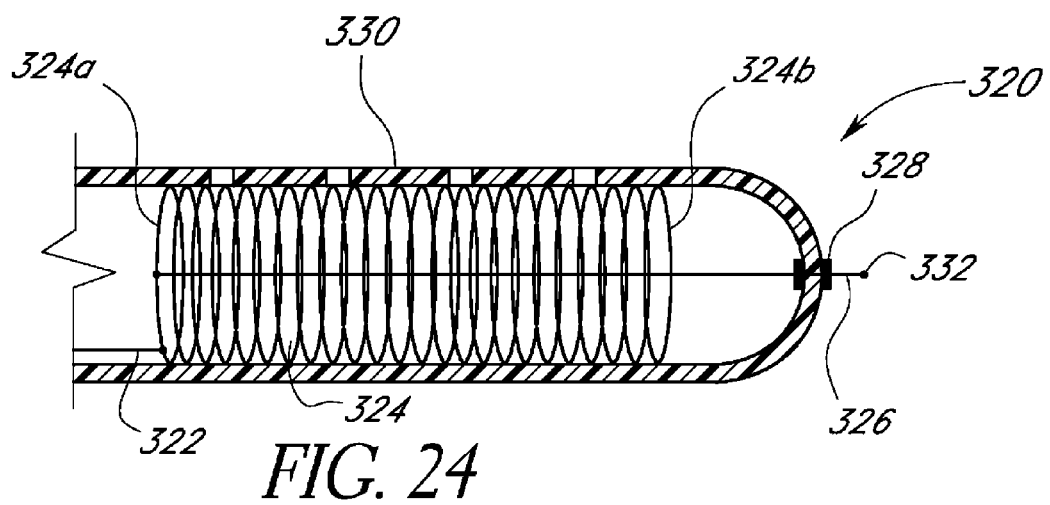
FIG. 24 is a cross-sectional view of another embodiment of a catheter.

An alternative embodiment of the catheter 320 is illustrated in FIG. 24. In this arrangement, the lead wire 322 can be attached to the proximal end 324a of the spring 324. The contact wire 326 can also be attached to the proximal end 324a of the spring 324, and passes through a sealed opening 326 at the distal end of the tube 330. In this configuration, the catheter 320, contact wire 326, and tip 322 operate similarly to the related components of catheter 300 described above except that, because the contact wire 326 does not attach to the distal end 346b of the spring 324, the movement of the coils of the distal spring 324 and, hence, the seepage of the fluid medication through the coils, will not be affected by any axial forces applied to the spring 324 by the contact wire 326 that may result when the tip 328 is in contact with body tissue after the catheter 320 is embedded in the body. In another alternative arrangement, the contact wire 326 can be attached to an intermediate portion of the spring 324.

Figure 25:
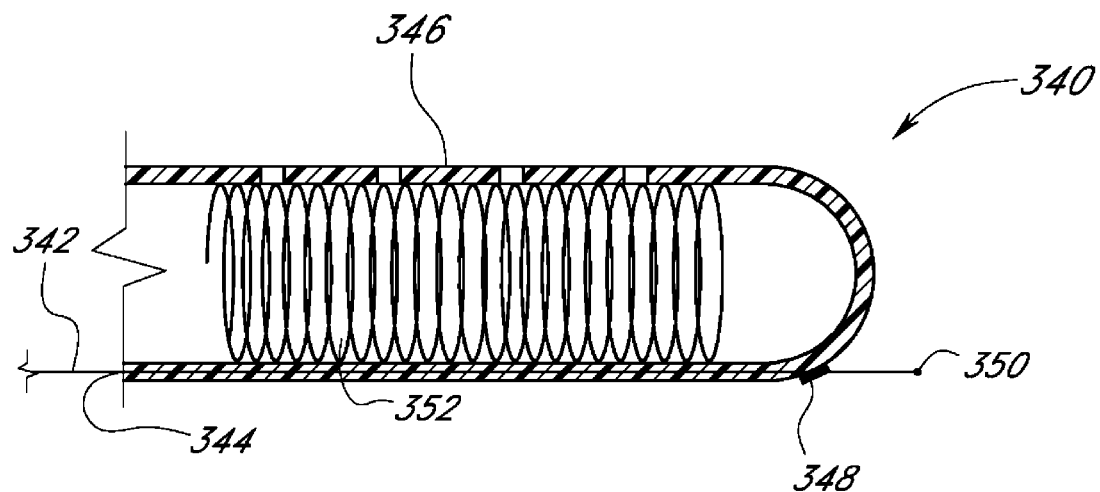
FIG. 25 is a cross-sectional view of another embodiment of a catheter.

Another embodiment of a catheter is illustrated in FIG. 25. In this arrangement, the catheter 340 can be configured so as to comprise a contact wire 342 that can pass through an opening 344 in the wall of the tube 346 and exit the tube 346 through an opening 348, which may or may not be sealed, in the distal end of the tube 346. In addition, the catheter 340 is not required to have an opening therein for passage of the contact wire 342. The contact wire 342 may, alternatively, be integrally formed into the wall of the catheter 340, i.e., the contact wire 342 can be embedded in the wall of the catheter 340 such that there is no opening in the wall of the catheter 340. For example, the catheter 340 and contact wire 342 may be integrated by a co-extrusion process. The tube 346 can be of any suitable configuration, including, but not limited to, the embodiments of the tubes described above. In some embodiments, the contact wire 342 can terminate at its distal end at or near the tip 350. The contact wire 342 can communicate directly with the preferably peripherally located nerve stimulation device, and can be insulated from the spring 352 and the tissue of the body by the wall of the tube 346 which can be made of an electrically insulating material. In some embodiments, only the distal portion of the contact wire 342 is exposed. In this configuration, the catheter 340, contact wire 342, and tip 350 operate similarly to the catheter 300 described above. Further, the contact wire 342 can preferably controllably slide in its axial direction within the opening 344 such that, after the catheter 340 is optimally positioned adjacent to the nerve plexus, the contact wire 342 can be retracted such that the tip 350 can be positioned adjacent to or within the sealed opening 348 so that the nerve plexus is not damaged by inadvertent contact with the contact wire 342 after the tube has been embedded in the body.

Figure 26:
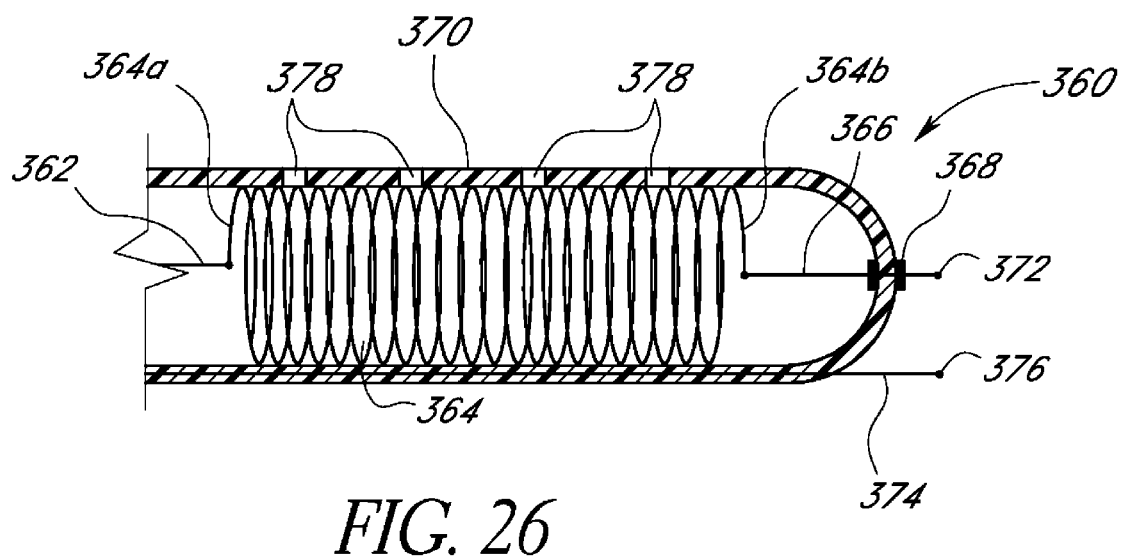
FIG. 26 is a cross-sectional view of another embodiment of a catheter.

Another embodiment of a catheter is illustrated in FIG. 26. In this arrangement, the catheter 360 can have an electrically conductive lead wire 362 that can be connected, integrally or otherwise, to the proximal end 364a of an electrically conductive coiled member or spring 364. The lead wire 362 passes through the catheter lumen of the type described above and removably attaches to a preferably peripherally located nerve stimulation device or generator by use of an alligator clip or other similarly configured connection device, as described above. A contact wire 366 can be attached to the distal end 364b of the spring 364 and passes through a sealed opening 368 located at the center portion of the distal end of the tube 370. The spring 364 helps stabilize the position of the contact wire 366 relative to the opening 368. Because the spring 364 can be electrically conductive, the electric pulse fed to the proximal end 364a of the spring by the nerve stimulation device through the lead wire 362 can be transmitted to the contact wire 366. The spring 364, lead wire 362, and contact wire 366 can be integrally formed from a single piece of electrically conductive wire. The tube 370 can be made of an electrically insulating material so that the electrical pulse transmitted through the lead wire 362, spring 364, and contact wire 366 does not transfer to any tissue of the body adjacent to the tube 370, except through the contact wire 366. The contact wire 366 can be coated with an insulating material at all points along the length of the contact wire 366 except for the tip 372 of the contact wire 366 to prevent leakage of the electrical pulse into body tissue located adjacent to the contact wire 366.

An electrically conductive ground wire 374, which can be embedded in the wall of the catheter 360, can also protrude from the distal end of the catheter tube 370 to provide a ground in the body for the nerve stimulation device. The ground wire 374, which may have a tip 376, can be connected to the external nerve stimulation device. The ground wire 374 can be removably attached to the nerve stimulation device. After the tube is positioned in the desired location, the nerve stimulation device can be disconnected from the lead wire 362 and ground wire 374. Although described as a lead wire 362 and a ground wire 374 for convenience, it will be appreciated that the wires 362, 374 can cooperate to form a portion of an electrical circuit and either wire 362, 374 can be connected to either of the positive or negative terminals of a nerve simulation device. In addition, both wires 362, 374 could be within the catheter tube 270, similar to the illustrated wire 374.

So configured, electrical stimulus can be transmitted from a peripheral nerve stimulation device to the tip 372 of the contact wire 366 that can be positioned within the catheter tube 370. The peripheral nerve stimulation device preferably sends intermittent electrical stimulus through the lead wire 362, spring 364, and contact wire 366 to the electrically conductive tip 372. The electrical pulse can be transmitted through the tip 372 into the tissue of the body, or nerve, to which it contacts or within close proximity to. The grounding wire 374 completes the electrical circuit for the nerve stimulation device so that the electrical pulse travels through the body's tissue proximally located to the tip 372 and through the grounding wire 374. The operation of the catheter 360 and nerve stimulation device to determine the proximity of the catheter 360 to the target nerve can be the same as described above with respect to catheter 300 illustrated in FIGS. 22-23. After the catheter 360 is positioned in the desired location, the tip 368 and contact wire 366 can be retracted by retracting the lead wire 362 back through the lumen far enough such that the tip 372 can be either adjacent to or inside of the sealed opening 368 and, also, such that all of the exit holes 378 can remain positioned adjacent to the spring 364.

Figure 27A:
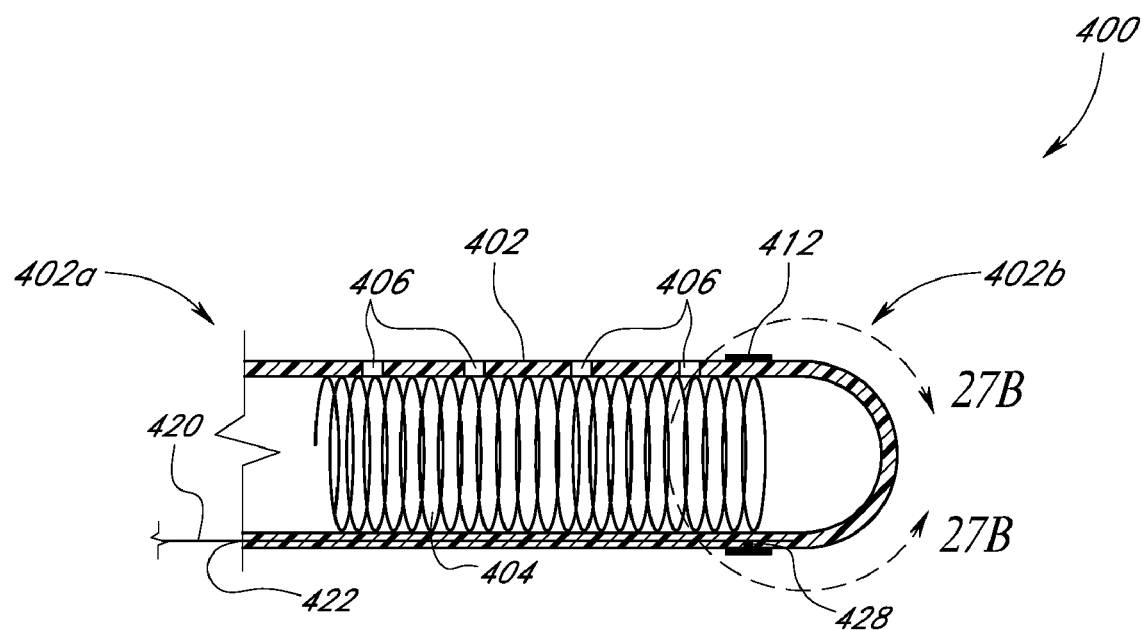
FIG. 27A is a cross-sectional view of another embodiment of a catheter.
Figure 27B:
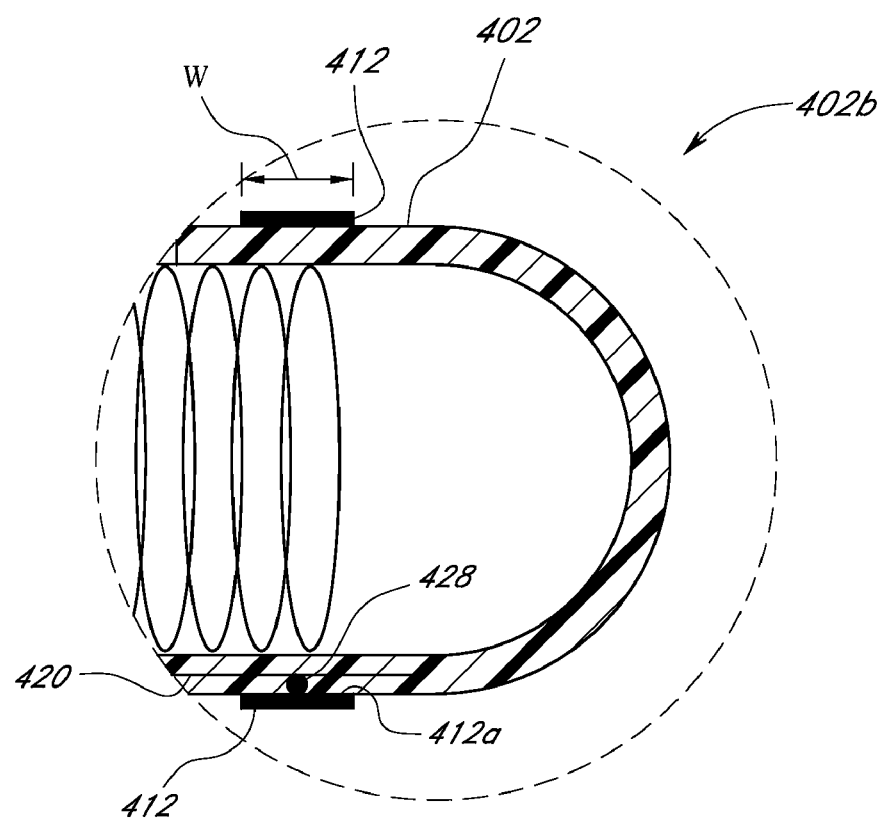
FIG. 27B is an enlarged cross-sectional view of the embodiment of a catheter illustrated in FIG. 27A, defined by curve 27B-27B.

FIG. 27A is a cross-sectional view of another embodiment of a catheter 400. FIG. 27B is an enlarged cross-sectional view of the embodiment of a catheter 400 illustrated in FIG. 27A, defined by curve 27B-27B. In some embodiments, the catheter 400 can comprise any of the components, features, materials, sizes, geometries, details, or configurations of any of the other catheters disclosed herein. In some embodiments, as in the illustrated embodiment, the catheter 400 can comprise a tube 402, a spring member 404, and openings 406 formed in the tube 402 similar to any of the tubes, springs, or openings described above. In some embodiments, as in the illustrated embodiment, the catheter 400 can be configured to comprise a conductive wire 420 that can pass through an opening 422 in the wall of the tube 402. However, the catheter 400 is not required to have an opening therein for passage of the wire 420. In some embodiments, the conductive wire 420 can be integrally formed with or embedded in the wall of the tube 402 such that there is no pre-existing opening in the wall of the catheter 400. One possibility for constructing such a catheter is by utilizing a co-extrusion process; which would embed the wire 420 in the catheter tube 402 during extrusion of the catheter tube 402. In the illustrated embodiment, the wire 420 can terminate near the distal end 402b of the tube 402. The wire 420 can communicate directly with the preferably peripherally located nerve stimulation device, and can be insulated from the spring 404 and the tissue of the body by the wall of the tube 402. Accordingly, in some embodiments, the tube 402 can be made of an electrically insulating material.

The tube 402 can be of any suitable configuration, including, but not limited to, the configuration of any of the embodiments of the tubes described above. In some embodiments, as in the illustrated embodiment, the catheter 400 can be configured such that the wire 420 is substantially completely encapsulated within the wall of the tube 402 so that no portion of the wire 420 projects out of the tube 402. In the illustrated embodiment, the wire 420 can terminate near the distal end 402b of the tube 402. A conductive band 412 can be positioned on the outside surface of a portion of the tube 402 at any desired position on the tube 402 and can be configured to be in electrical communication with the conductive wire 420. In some embodiments, as in the illustrated embodiment, the conductive band 412 can be an annular band of electrically conductive material defining a width (represented by "W" in FIG. 27B) that can be between approximately 0.05 in. or less and approximately 0.2 in. or more, or between approximately 0.1 in. and approximately 0.15 in. In some embodiments, the thickness of the band 412 can be approximately 0.001 in. or less, or between approximately 0.001 in. and approximately 0.05 in. or more, or between approximately 0.005 in. and approximately 0.015 in. However, the size of the band 412 is not limited to the dimensions listed above. The band 412 can define any suitable or desired thickness or width either within or outside of the above listed dimensional ranges.

In some embodiments, a projection 428 can be formed on a portion of the inside surface 412a of the band 412 and the catheter 400 can be configured such that, when the band 412 is assembled with the tube 402, the projection 428 can provide an electrical connection between the conductive wire 420 and the conductive band 412. In some embodiments, the projection 428 can be a conical projection formed on a portion of the inside surface 412a of the band 412. In some embodiments, the projection 428 can be an annular ridge formed on a portion of the inside surface 412a of the band 412.

In some embodiments, an opening (not illustrated) can be formed in the tube 402 between the conductive wire 420 and the band 412 through which the projection 428 can pass. In some embodiments, the projection 428 can be configured so as to penetrate through the wall of the tube 402 to make contact with the conductive wire 420 when the band 412 is positioned around the outside surface of the tube 402. Additionally, in some embodiments, the tube 402 can define a recess, an annular channel or otherwise be configured such that, when the band 412 is assembled with the tube 402, the inside surface 412a of the band 412 can directly contact the conductive wire 420. For example, when an annular channel is utilized, a portion of the inside surface 412a of the band 412 other than the projection 428 may be in contact with the conductive wire 420 such that the projection 428 is not required. The recess, annular channel or other structure or mechanism for providing access to the conductive wire 420 may be created during or after formation of the catheter tube 402 and wire 420 assembly. For example, the recess, annular channel or other access structure or mechanism may be created by a suitable material removal process (e.g., chemical etching, laser ablation, mechanical material removal, etc.). Moreover, once access to the wire 420 is gained, the wire 420 may be manipulated (e.g., pulled out of the recess, annular channel or other access structure or mechanism) relative to the tube 402 such that an end portion of the wire 420 can protrude radially from the catheter tube 402. In some embodiments, the conductive band 412 can be formed of stainless steel, or any other suitable conductive material. Additionally, in some embodiments, the band 412 can be formed from a radiopaque material that can enable a medical practitioner to determine the location of band 412 and, accordingly, the tube 402', in fluoroscopy or during any other suitable or desired imaging technique.

The band 412 can be assembled with the tube 402 by any desired or suitable means. For example, in some embodiments, the band 402 can be positioned in the desired location around the outside surface of the tube 402 and then be reduced in diameter, such as by a swaging process. This preferably results in a tight fit around the outside of the tube 402 so that the band 402 remains in the desired location on the tube 402. Additionally, in some embodiments, the tube 402 can be stretched prior to being assembled with the band 412 so as to decrease the cross-sectional size of the tube 402. Once the band 412 is positioned in the desired location relative to the tube 402, the tube 402 can be relaxed so that the cross-sectional size of the tube 402 expands to its relaxed size, preferably resulting in a tight or interference fit with the band 412. Additionally, in the embodiments where the tube 402 comprises a projection 428, it is preferable that the band 412 be positioned on the tube 402 such that the projection 428 aligns with and contacts conductive wire 421 when the band 412 is assembled with the tube 402.

In some embodiments, because the band 412 can be in electrical communication with the conductive wire 420, the band 412 will preferably provide an electrical stimulus to tissue surrounding the outside of the catheter 400 when such electrical stimulus is provided to the wire 420. In some embodiments, the band 412 can be configured so as to provide an electrical stimulus in a radial array from the outside surface of the catheter 400. In some embodiments, an insulating or masking material can be applied to portions of the band 412 so that portions of the band 412 do not transmit an electrical stimulus to the tissue surrounding the catheter 400.

Figure 28A:
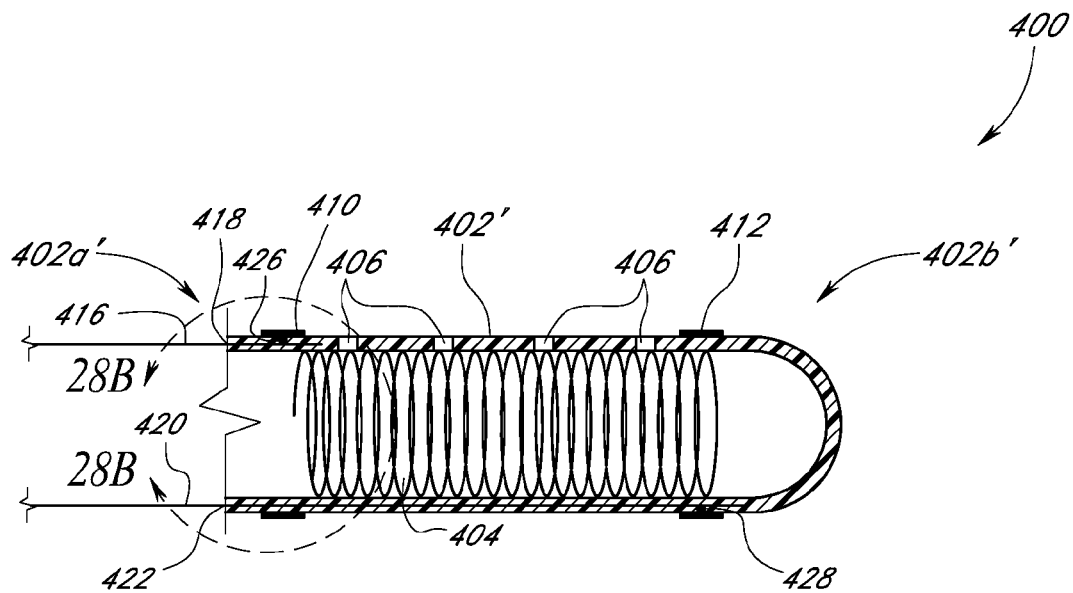
FIG. 28A is a cross-sectional view of another embodiment of a catheter.
Figure 28B:
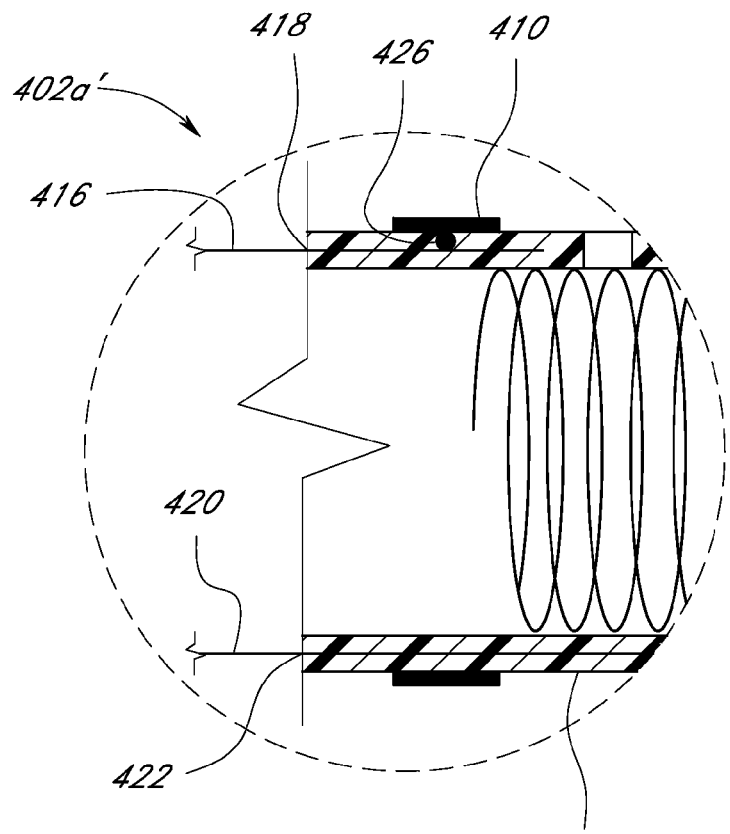
FIG. 28B is an enlarged cross-sectional view of the embodiment of a catheter illustrated in FIG. 28A, defined by curve 28B-28B.

FIG. 28A is a cross-sectional view of another embodiment of a catheter 400'. FIG. 28B is an enlarged cross-sectional view of the embodiment of a catheter illustrated in FIG. 28A, defined by curve 28B-28B. In some embodiments, the catheter 400' can comprise any of the components, features, materials, sizes, geometries, details, or configurations of any of the other catheters disclosed herein, including but not limited to the catheter 400 described above. In some embodiments, as in the illustrated embodiment, the catheter 400' can comprise a tube 402', a spring member 404, and openings 406 formed in the tube 402' similar to any of the tubes, springs, or openings described above.

In some embodiments, the catheter 400' can be the same as the catheter 400 described above, and can further comprise the features and components described below. With reference to FIGS. 28A and 28B, in addition to comprising a first conductive wire 420 and first conductive band 412, as described above, positioned near the distal end 402b of the tube 402, the catheter 400' can be configured to comprise a second conductive wire 416 that can pass through an opening 418 in the wall of the tube 402' that is in electrical communication with a second band 410 positioned near the proximal end 402a' of the tube 402'. In some embodiments, the catheter 400' is not required to have an opening therein for passage of the wire 416. In some embodiments, the second conductive wire 416 can be integrally formed with or embedded in the wall of the tube 402' such that there is no opening in the wall of the catheter 400'. In some embodiments, the bands 410 and 412 can be positioned at any desired location on the tubes 402 or 402' in addition to the positions illustrated in FIGS. 28A and 28B.

The tube 402' can be of any suitable configuration, including, but not limited to, the configuration of any of the embodiments of the tubes described above. In some embodiments, as in the illustrated embodiment, the catheter 400' can be configured such that the wire 416 is substantially completely encapsulated within the wall of the tube 402' so that no portion of the wire 416 projects out of the tube 402'. The second conductive band 410 can be positioned on the outside surface of a portion of the tube 402' and can be configured to be in electrical communication with the second conductive wire 416. As shown in FIGS. 28A and 28B, in the illustrated embodiment, the wire 416 can terminate just aft of the desired position of the second band 410. In some embodiments, as in the illustrated embodiment, the second conductive band 410 can be an annular band of electrically conductive material similar in size, shape, material, and other details as compared to the first conductive band 412 described above. Additionally, in some embodiments, the catheter 400' can be configured so that second conductive band 410 can be assembled with the tube 402' by any suitable means, including but not limited to, the means described above with reference to the first conductive band 412 and the catheter 400.

In some embodiments, a projection 426 can be formed on a portion of the inside surface 410a of the second band 410 and the catheter 400' can be configured such that, when the second band 410 is assembled with the tube 402', the projection 426 can provide an electrical connection between the second conductive wire 416 and the second conductive band 410. In some embodiments, the projection 426 can be a conical projection formed on a portion of inside surface 410a of the second band 410. In some embodiments, the projection 426 can be an annular ridge formed on a portion of the inside surface 410a of the second band 410.

In some embodiments, an opening (not illustrated) can be formed in the tube 402' between the second conductive wire 416 and the second band 410 through which the projection 426 can pass. In some embodiments, the projection 426 can be configured so as to penetrate through the wall of the tube 402' to make contact with the second conductive wire 416 when the second band 410 is positioned around the outside surface of the tube 402'. Additionally, in some embodiments (not illustrated), the tube 402' can define a recess, an annular channel or otherwise be configured such that, when the second band 410 is positioned on the tube 402', the inside surface 410a of the second band 410 other than the projection 426 can directly contact the second conductive wire 416 such that the projection 426 is not required.

In the illustrated embodiment, the catheter 400' can be configured such that the first conductive band 412 is in electrical communication with the first conductive wire 420 but not in electrical communication with the second conductive wire 416. Similarly, in the illustrated embodiment, the catheter 400' can be configured such that the second conductive band 410 is in electrical communication with the second conductive wire 416 but not in electrical communication with the first conductive wire 420. The wire 416 can communicate directly with a preferably peripherally located nerve stimulation device or generator, and can be insulated from the spring 404 and the tissue of the body by the wall of the tube 402'. Accordingly, in some embodiments, the tube 402' can be made of an electrically insulating material.

Additionally, in some embodiments, the first conductive wire 420 can be electrically isolated from or independent as compared to the second conductive wire 416. In this configuration, in operator can provide an electrical stimulus to the first conductive band 412 independent of the electrical stimulus that can be provided to the second conductive band 410, and vice versa. By independently providing an electrical stimulus to the tissue surrounding the catheter 400' through either the first conductive band 412 or the second conductive band 410, the medical practitioner or operator can more accurately determine the location of the tube 402' or the infusion section of the tube 402' and relative to the nerve plexus or desired location by analyzing the result of the nerve stimulation provided by either the first conductive band 412 or the second conductive band 410. For example, use of the two electrically conductive bands 410 and 412 described above can permit the medical practitioner to determine whether the proximal end 402a' or the distal end 402b' is closer to the nerve or nerve plexus by comparing the result of the nerve stimulation. The practitioner can then alter the position of the tube 402' and repeat the stimulation process in whole or in part until a desired position of the tube 402' is achieved.

However, in some embodiments, the first conductive wire 420 can be in electrical communication with the second conductive wire 416 so that the first band 412 is in electrical communication with the second band 410. In this configuration, the medical practitioner or operator can provide an electrical stimulus through the first band 412 and the second band 410 simultaneously. In some embodiments, the first and second conductive bands 412, 410 can define any other suitable shape. Further, the catheter 400' can be configured such that one or more additional conductive bands or elements are assembled with the catheter tube 402'.

With regard to all of the above embodiments of catheters, an independent guide wire lumen can be provided within or adjacent to the lumen(s) disclosed, as will be understood by those skilled in the art.

As will be easily understood by those of skill in the art, any of the catheter embodiments described herein can be used in a variety of applications including, but not limited to, peripheral nerve blocks, intrathecal infusions, epideral infusions, intravascular infusions, intra-arterial infusions and intraarticular infusions, as well as in wound site pain management.

In addition, any of the catheters disclosed herein can be integral with a fluid line emanating from an infusion pump as opposed to being an independent catheter designed to be connected or secured to an infusion pump.

Although this invention has been disclosed in the context of certain preferred embodiments and examples, it will be understood by those skilled in the art that the present disclosure extends beyond the specifically disclosed embodiments to other alternative embodiments and/or uses of the invention and obvious modifications and equivalents thereof. Thus, it is intended that the scope of the present disclosure herein disclosed should not be limited by the particular disclosed embodiments described above, but should be determined only by a fair reading of the claims that follow.

What is claimed is:

1. An apparatus for the delivery of a fluid to an anatomical region, the apparatus comprising:
    a catheter comprising a catheter body, the catheter body comprising a lumen therein, a closed radiused distal end defined by a continuous, unbroken distal portion of the catheter body wherein the catheter body extends to the closed distal end, and an infusion section configured to permit fluid to pass through the catheter body, the infusion section defining a length that is less than a length of the catheter body;
    a coiled member enclosed within the catheter body and the closed radiused distal end, the coiled member comprising adjacent coils and defining a first end, a second end, and a lumen therethrough, wherein the second end of the coiled member is positioned nearer to the distal end of the catheter body than the first end of the coiled member; and
    one or more electrically conductive elements supported by the catheter body and capable of electrical communication with one or more sources of electrical stimulus located peripheral to the catheter body for providing an electrical stimulus to a patient's tissue surrounding the catheter body;
    wherein:
    the coiled member is configured such that, when the coiled member is in a relaxed position, at least a portion of an outer surface of the adjacent coils are in contact with one another in at least a portion of the coiled member;
    the coiled member has a length that is greater than or equal to the length of the infusion section when the coiled member is in the relaxed position;
    the coiled member is capable of conducting an electrical stimulus; and
    the apparatus is configured such that fluid must pass between one or more adjacent coils of the coiled member before passing through the infusion section
    at least one of the one or more electrically conductive elements is in communication with the coiled member.

2. The apparatus of claim 1, wherein the catheter body defines a generally elongate, tubular shape.

3. The apparatus of claim 1, wherein the infusion section of the catheter body comprises a plurality of openings in the catheter body.

4. The apparatus of claim 1, wherein at least one of the one or more electrically conductive elements is an electrically conductive wire.

5. The apparatus of claim 4, wherein the conductive wire is embedded in a wall of the catheter body adjacent the distal end of the apparatus.

6. The apparatus of claim 4, wherein the conductive wire projects from the catheter body so as to extend beyond the outside surface of the catheter body adjacent the distal end of the apparatus.

7. The apparatus of claim 1, wherein at least one of the one or more electrically conductive elements is an electrically conductive band concentrically contacting a portion of the outside surface of the catheter body.

8. The apparatus of claim 1, wherein the one or more electrically conductive elements comprises a first electrically conductive band concentrically contacting a first portion of the outside surface of the catheter body and a second electrically conductive band concentrically contacting a second portion of the outside surface of the catheter body, wherein the first portion of the outside surface of the catheter body is separate from the second portion of the outside surface of the catheter body.

9. The apparatus of claim 8, wherein the catheter is configured such that an electrical stimulus can be provided through the first electrically conductive band without providing an electrical stimulus through the second electrically conductive band, or through the second electrically conductive band without providing an electrical stimulus through the first electrically conductive band.

10. The apparatus of claim 1, wherein the coiled member is capable of conducting an electrical stimulus, the one or more electrically conductive elements comprises a first and second conductive elements the first conductive element is in communication with the first end of the coiled member and is configured to communicate with an electric stimulus generating device and the second conductive element is in communication with the second end of the coiled member and is configured to project from the catheter body.

11. The apparatus of claim 10, wherein the second conductive element projects from the distal end of the catheter body.

12. The apparatus of claim 1, wherein at least one of the one or more electrically conductive elements comprises stainless steel.

13. A catheter for the delivery of a fluid to an anatomical region, the catheter comprising:
- a catheter body comprising a lumen therein, a closed radiused distal end defined by a continuous, unbroken distal portion of the catheter body wherein the catheter body extends to the closed distal end, and an infusion section configured to permit fluid to pass through the catheter body in a controlled manner, the infusion section having a first and second end and a length that is less than a length of the catheter body;
- a first electrically conductive element supported by the catheter body and positioned adjacent to the first end of the infusion section, the first conductive element being configured to transmit a first electrical stimulus to an object located external to the catheter body; and
- a second electrically conductive element supported by the catheter body and positioned adjacent to the second end of the infusion section, the second conductive element being configured to transmit a second electrical stimulus to an object located external to the catheter body, wherein:
  - the first and second conductive elements are each configured to be connectable to a source of electrical stimulus external to the catheter;
  - the first conductive element is located on the catheter body at a position that is different than the position of the second conductive element; and
  - the first conductive element and the second conductive element are embedded into the catheter body and extend radially outward beyond the catheter body.

14. The catheter of claim 13, wherein the catheter is configured such that an electrical stimulus can be transmitted through the first conductive element without transmitting an electrical stimulus through the second conductive element, or through the second conductive element without transmitting an electrical stimulus through the first conductive element.

15. The catheter of claim 13, further comprising a conductive wire in communication with at least one of the first and second conductive elements.

16. The catheter of claim 13, further comprising a coiled member positioned within the lumen of the catheter body.

17. The catheter of claim 13, wherein the infusion section of the catheter body comprises a plurality of openings in the catheter body.

18. The catheter of claim 13, wherein at least one of the first and second electrically conductive elements comprises an electrically conductive annular band embedded into the catheter body extending radially outward beyond the catheter body.

* * * * *